(12) United States Patent
Troy

(10) Patent No.: US 9,376,466 B2
(45) Date of Patent: Jun. 28, 2016

(54) PEPTIDE INHIBITORS OF CASPASE 2 ACTIVATION

(71) Applicant: The Trustees of Columbia University in the city of New York, New York, NY (US)

(72) Inventor: Carol M. Troy, Hastings-on-Hudson, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/201,132

(22) Filed: Mar. 7, 2014

(65) Prior Publication Data

US 2015/0148302 A1   May 28, 2015

Related U.S. Application Data

(63) Continuation of application No. PCT/US2012/054269, filed on Sep. 7, 2012.

(60) Provisional application No. 61/532,717, filed on Sep. 9, 2011.

(51) Int. Cl.
*C07K 7/06* (2006.01)
*A61K 38/00* (2006.01)

(52) U.S. Cl.
CPC .. *C07K 7/06* (2013.01); *A61K 38/00* (2013.01)

(58) Field of Classification Search
None
See application file for complete search history.

(56) References Cited

U.S. PATENT DOCUMENTS

2003/0092659 A1* 5/2003 Troy et al. ........................ 514/44
2009/0042805 A1* 2/2009 Chauvier ............... C07K 5/101
514/20.1

OTHER PUBLICATIONS

Droin 2000 "Identification of a caspase-2 isoform that behaves as an endogenous inhibitor of the caspase cascade" Cancer research 60: 7039-7047.*
Uniprot 2016 "P$2575: Caspase 2 Human" accessed from uniprot. org on Feb. 23, 2016.*

* cited by examiner

*Primary Examiner* — Adam M Weidner
(74) *Attorney, Agent, or Firm* — Baker Botts L.L.P.

(57) ABSTRACT

The present invention relates to compositions, including membrane permeable complexes, comprising a Caspase 2 activation inhibitory peptide having the amino acid sequence AFDAFC as well as methods of using the same for the treatment of neurodegenerative conditions associated with apoptosis in the central nervous system, such as Alzheimer's Disease, Mild Cognitive Impairment, Parkinson's Disease, amyotrophic lateral sclerosis, Huntington's chorea, and Creutzfeld-Jacob disease.

6 Claims, 25 Drawing Sheets

Figure 1:
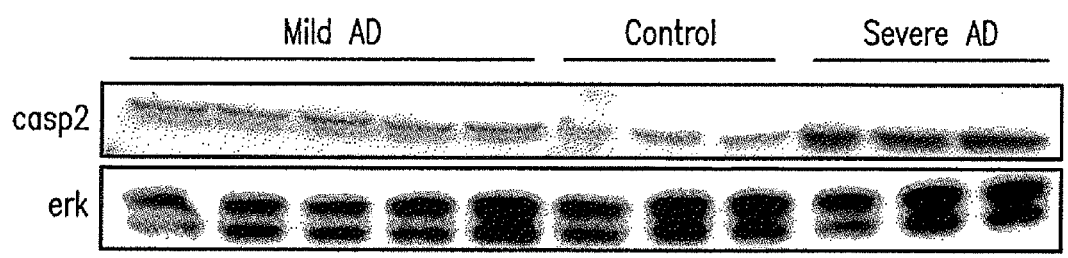

Lysates of entorhinal cortex of patients with mild AD, severe AD and control subjects were analyzed by Western blotting for casp2, Erk is the loading control.

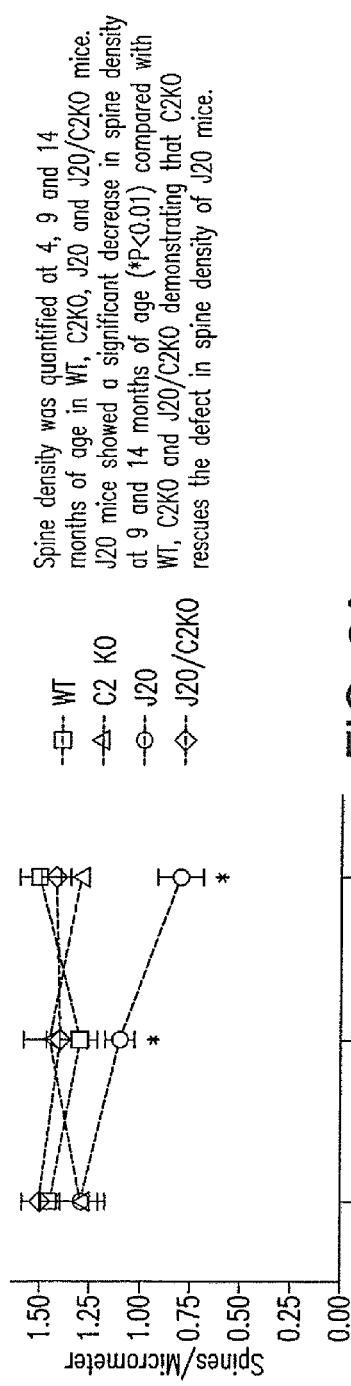

FIG. 2A

Spine density was quantified at 4, 9 and 14 months of age in WT, C2KO, J20 and J20/C2KO mice. J20 mice showed a significant decrease in spine density at 9 and 14 months of age (*P<0.01) compared with WT, C2KO and J20/C2KO demonstrating that C2KO rescues the defect in spine density of J20 mice.

FIG. 2B

Mice from the four different genotypes were tested in the radial-arm water-maze for spatial working memory at ages of 4 and 14 months. In the last of 5 trials, 4 month old J20 mice showed a memory deficit compared with WT, Casp2KO and J20/Casp2KO littermates *P<0.01.

FIG. 2C

Mice from the four different genotypes were tested in the radial-arm water-maze for spatial working memory at ages of 4 and 14 months. This deficit persisted at 14 months of age (*P<0.01).

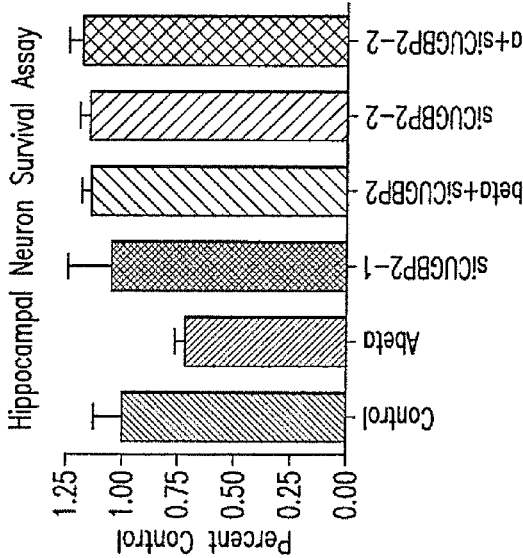
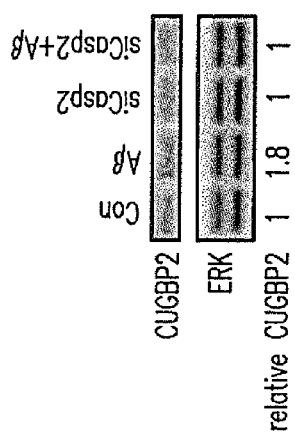
FIG. 3A
FIG. 3B
CUGBP2, a novel gene product linked to LOAD, is regulated by casp2 and required for Aβ42 neuronal death.
Hippocampal neurons treated with 3 μM Aβ42 for 4hrs with and without the indicated Pen1-siRNA. CUGBP2 levels were determined by Western blotting and cell survival was quantified in B. Both siRNA sequences to CUGBP2 gave 85% knockdown of protein expression.

PIDD null neurons are sensitive to Aβ or TFD
Active caspase-2 is induced in PIDD null neurons by TFD Cultures were treated with 50μM bVAD for 2hrs and then TFD
for 1hr and bVAD-casp2 complexes were analyzed by Western blotting.

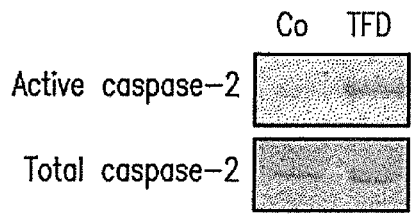

Active caspase-2

Total caspase-2

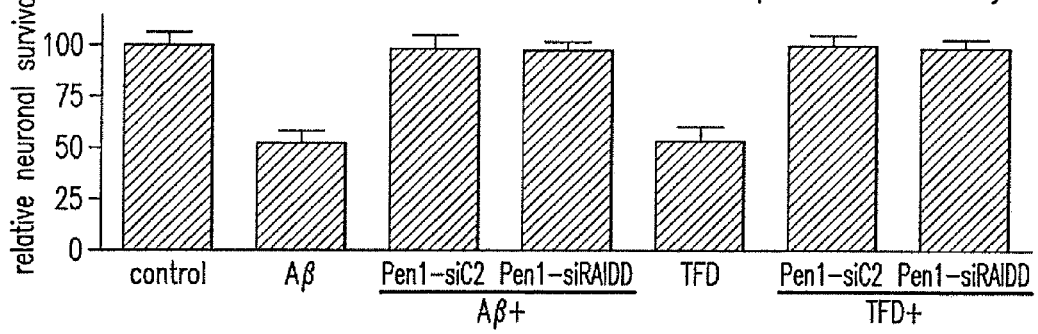

Primary neurons from PIDD null mice were treated with 3μM Aβ42
or TFD and indicated Pen1-siRNA. Survival was quantified at 1 day.

FIG. 5

PEPTIDE INHIBITORS OF CASPASE 2 ACTIVATION

CROSS REFERENCE TO RELATED APPLICATIONS

The present application is a continuation of PCT application PCT/US12/054269, filed Sep. 7, 2012, which claims priority to U.S. Provisional Application No. 61/532,717, filed on Sep. 9, 2011, the disclosures of both of which are incorporated by reference herein in their entirety.

STATEMENT REGARDING FEDERALLY-SPONSORED RESEARCH

This invention was made with government support under Grant No. NS035933 awarded by the National Institutes of Health. The government has certain rights in the invention.

SEQUENCE LISTING

The specification further incorporates by reference the Sequence Listing submitted via EFS on Aug. 4, 2014. Pursuant to 37 C.F.R. §1.52(e)(5), the Sequence Listing text file, identified as 0700505137SEQLIST.txt, is 3,786 bytes in size and was created on Aug. 4, 2014. The Sequence Listing, electronically filed on Aug. 4, 2014, does not extend beyond the scope of the specification and thus does not contain new matter.

1. INTRODUCTION

The present invention relates to compositions, including membrane permeable complexes, comprising a Caspase 2 activation inhibitory peptide having the amino acid sequence AFDAFC, as well as methods of using the same for the treatment of neurodegenerative conditions associated with apoptosis in the central nervous system, such as Alzheimer's Disease, Mild Cognitive Impairment, Parkinson's Disease, amyotrophic lateral sclerosis, Huntington's chorea, and Creutzfeld-Jacob disease.

2. BACKGROUND OF THE INVENTION

Over a hundred years ago Alois Alzheimer identified the clinical and pathologic hallmarks of a dementing illness that came to be known as Alzheimer's Disease (AD). (Alzheimer, et al., An English translation of Alzheimer's 1907 paper, "Uber eine eigenartige Erkankung der Hirnrinde", Clin Anat 8 (6), 429-431 (1995)). AD is characterized clinically by progressive loss of cognition and pathologically by the accumulation of amyloid plaques, neurofibrillary tangles, synaptic loss and neuronal death. It is estimated that patients already have lost as much as 50% of their neurons at the time of their first clinical symptoms, supporting the relevance of neuronal death in the disease. (DeKosky, et al., Revision of the criteria for Alzheimer's disease: A symposium, Alzheimers Dement 7 (1), e1-12 (2011)). In the century since Alzheimer's studies, β-amyloid and tau were identified as the protein components of plaques and tangles respectively, and genetic studies of familial AD identified mutations in genes regulating the production of Aβ, supporting a critical role for Afβ in the disease. (Li, et al., beta-Amyloid protein-dependent nitric oxide production from microglial cells and neurotoxicity, Brain Res 720 (1-2), 93-100 (1996); Kruman, et al., Evidence that 4-hydroxynonenal mediates oxidative stress-induced neuronal apoptosis J Neurosci 17 (13), 5089-5100 (1997); Pike, et al., Beta-amyloid neurotoxicity in vitro: evidence of oxidative stress but not protection by antioxidants, J Neuroehem 69 (4), 1601-1611 (1997); Keller, et al., Mitochondrial manganese superoxide dismutase prevents neural apoptosis and reduces ischemic brain injury: suppression of peroxynitrite production, lipid peroxidation, and mitochondrial dysfunction J Neurosci 18 (2), 687-697 (1998); and Guo, et al., Increased vulnerability of hippocampal neurons from presenilin-1 mutant knock-in mice to amyloid beta-peptide toxicity: central roles of superoxide production and caspase activation, J Neurochem 72 (3), 1019-1029 (1999)). More recently, Caspase 2 has been identified as a key factor in the role played by Afβ in AD and in neuronal dysfunction generally. (Reviewed in, Troy and Ribe, Caspase 2: Vestigial Remnant or Master Regulator?, Sci. Signal., 1 (38), e42 (2008)).

The significance of Caspase 2 as a critical mediator of neuronal dysfunction and death in AD is supported by several lines of evidence. First, brain tissue from patients with mild and severe AD shows increased expression of Caspase 2 when compared to age-matched controls (FIG. 1). Similarly, the neurological deficits of J20 hAPP mice, which exhibit age-related spine loss and cognitive dysfunction, can be blocked when the mice are engineered to lack Caspase 2 (FIG. 2). (Pozueta, et al., Caspase 2 is required for Abeta induced spine loss, American Soc. for Cell Biology Annual meeting (2010)). A further connection between Caspase 2 and AD is provided by studies of CUGBP2, a gene product that has been linked to late-onset AD. (Wijsman, et al., Genome-wide association of familial late-onset Alzheimer's disease replicates BIN1 and CLU and nominates CUGBP2 in interaction with APOE PLoS Genet 7 (2), e1001308 (2011)). Specifically, it has been found that CUGBP2 is induced by Aβ42 in a Caspase 2-dependent manner and is required for Aβ42 mediated death (FIG. 3). Taken together these data provide compelling evidence for an Aβ-induced Caspase 2-mediated pathway of neuronal dysfunction in AD.

Caspase 2 contains a long prodomain with a "caspase recruitment domain" (CARD). Activation of Caspase 2 requires dimerization via the CARD. 0 (RIP-associated ICH-1/CED-3-homologous protein with a death domain) contains a CARD and has been shown to function as an adaptor for Caspase 2. In non-neuronal cells, phosphorylation of Ser-140 in the prodomain of Caspase 2 has been shown to inhibit Caspase 2 activation. (Nutt, et al., Metabolic regulation of oocyte cell death through the CaMKII-mediated phosphorylation of Caspase 2, Cell 123 (1), 89-103 (2005); and Shin, et al., Caspase 2 primes cancer cells for TRAIL-mediated apoptosis by processing procaspase-8, Embo J 24 (20), 3532-3542 (2005)). Presumably such inhibition is achieved by blocking the interaction between Caspase 2 and RAIDD.

Figure 4:
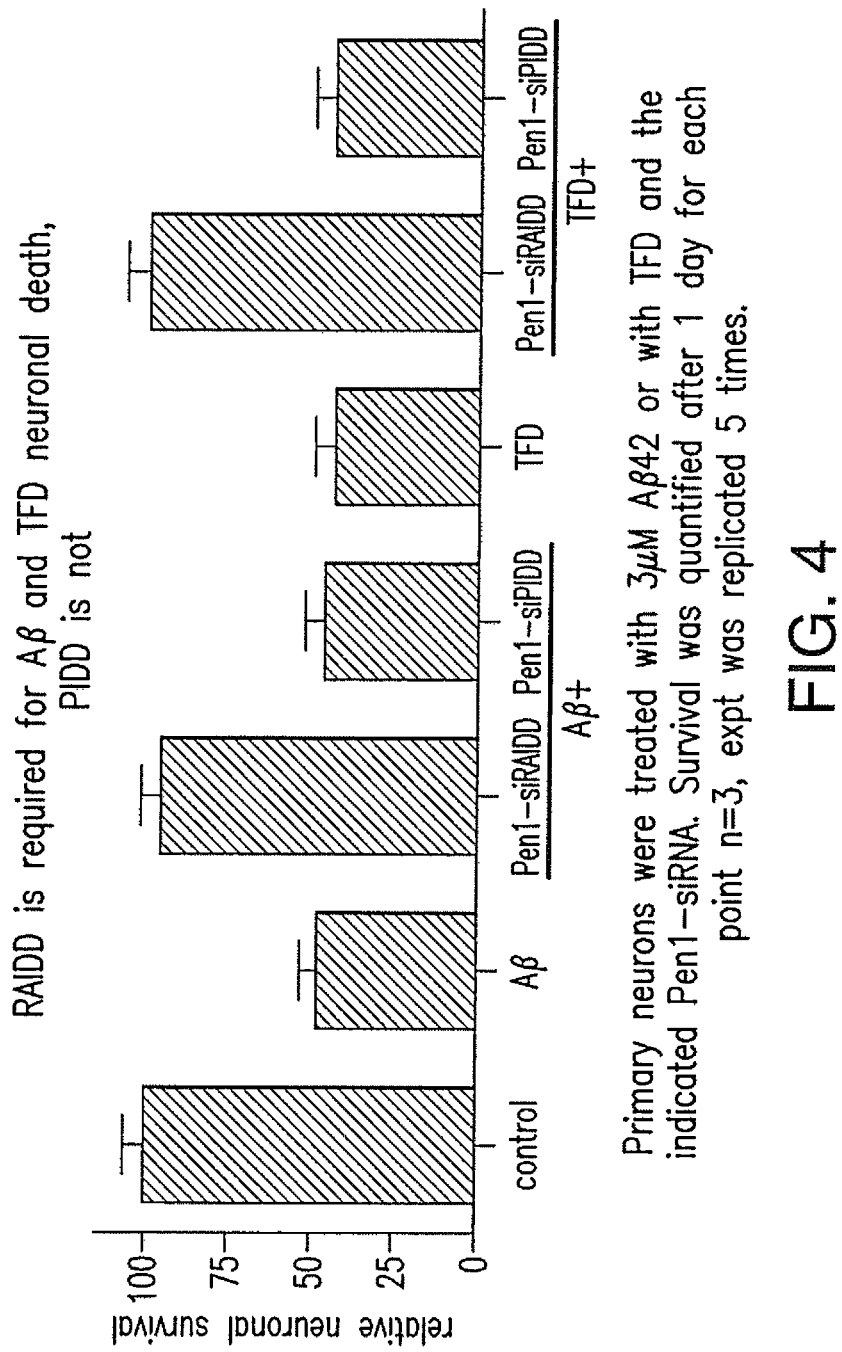

The activation complex for Caspase 2 has been proposed to be the PIDDosome, comprised of Caspase 2, RAIDD and PIDD. (Tinel, et al., The PIDDosome, a protein complex implicated in activation of Caspase 2 in response to genotoxic stress, Science 304 (5672), 843-846 (2004)). However, two independent studies of different lines of PIDD null mice suggest that non-neuronal death does not require PIDD. (Manzi, et al., Caspase 2 activation in the absence of PIDDosome formation, J Cell Biol 185 (2), 291-303 (2009); and Kim, et al., DNA damage- and stress-induced apoptosis occurs independently of PIDD, Apoptosis: an international journal on programmed cell death 14 (9), 1039-1049 (2009)). In addition, when Pen1-siRNAs capable of effectively targeting the destruction of PIDD and RAIDD mRNAs are employed, knockdown or knockout of PIDD does not block Caspase 2-dependent death (FIGS. 4 and 5). Thus, while PIDD is not critical for activation of Caspase 2 in neurons, RAIDD is required for Caspase 2-dependent neuronal death.

There remains a need in the field for compositions capable of robust and specific inhibition of Caspase 2-associated neuronal dysfunction. The present invention addresses this need by the development of a novel inhibitor of the Caspase 2/RAIDD interaction, and membrane permeable complexes thereof, which function to inhibit Caspase 2 activation.

3. SUMMARY OF THE INVENTION

In certain embodiments, the instant invention is directed to the Caspase 2 activation inhibitory peptide having the amino acid sequence AFDAFC (SEQ ID NO: 1). In certain embodiments, the instant invention is directed to compositions comprising the Caspase 2 activation inhibitory peptide.

In certain embodiments the present invention is directed to the Caspase 2 activation inhibitory peptide conjugated to a cell-penetrating peptide, optionally via a linker molecule.

In certain embodiments, the instant invention is directed to compositions comprising the Caspase 2 activation inhibitory peptide conjugated to a cell-penetrating peptide, wherein the cell-penetrating peptide is selected from the group consisting of penetratin1 ("Pen1"), transportan, pIS1, Tat(48-60), pVEC, MAP, and MTS. In certain embodiments, the instant invention is directed to the Caspase 2 activation inhibitory peptide conjugated to Pen1 ("AFDAFC-Pen1").

In certain embodiments, the instant invention is directed to methods of treating neurodegenerative conditions comprising administering, intranasally, an effective amount of the Caspase 2 activation inhibitory peptide to a subject in need thereof, wherein the neurodegenerative conditions is treated by such administration.

In certain embodiments, the instant invention is directed to methods of treating neurodegenerative conditions comprising administering, intranasally, an effective amount of the Caspase 2 activation inhibitory peptide to a subject in need thereof, wherein the Caspase 2 activation inhibitory peptide is conjugated to a cell-penetrating peptide.

In certain embodiments, the instant invention is directed to methods of inhibiting apoptosis in the central nervous system comprising administering, intranasally, an effective amount of the Caspase 2 activation inhibitory peptide to a subject in need thereof. For example, such inhibition is a modality of treating a neurodegenerative condition associated with apoptosis (that is to say, a method of inhibiting neurodegeneration) in the central nervous system, such as Alzheimer's Disease, Mild Cognitive Impairment, Parkinson's Disease, amyotrophic lateral sclerosis, Huntington's chorea, and Creutzfeld-Jacob disease. In various related non-limiting embodiments, the Caspase 2 inhibitory peptide is conjugated to a cell-penetrating peptide such as, but not limited to, Pen1, transportan, pIS1, Tat(48-60), pVEC, MAP, or MTS.

4. BRIEF DESCRIPTION OF THE FIGURES

FIG. 1 depicts the results of experiments comparing Caspase 2 protein expression in brain tissue from patients with mild and severe AD and age-matched controls. Lysates of entorhinal cortex of patients and control subjects were analyzed by western blotting for Caspase 2 ("casp2") and "erk" is the loading control.

FIGS. 2A-2C depict the blockage of the neurological deficits of J20 hAPP mice, which exhibit age-related spine loss and cognitive dysfunction, when Caspase 2 is knocked-out. A. Spine density was quantified at 4, 9, and 14 months of age in Wild Type (WT), Caspase 2-Knock Out (C2KO), J20, and J20/C2KO mice. B. Mice from the four different genotypes were tested in the radial-arm water-maze for spatial working memory at age 4 months. C. The memory deficit identified in B persists in mice at 14 months of age.

FIGS. 3A-3B depict results of experiments indicating that CUGBP2, a novel gene product linked to Late Onset AD ("LOAD"), is regulated by Caspase 2 ("casp2") and required for Aβ42 neuronal death. A. Hippocampal neurons treated with 3 μM Aβ42 for 4 hrs, with and without the indicated Pen1-siRNA. CUGBP2 levels were determined by western blotting and cell survival was quantified in B.

FIG. 4 depicts results of experiments indicating that RAIDD is required for Aβ and Trophic Factor Deprivation ("TFD") neuronal death, while PIDD is not. Primary neurons were treated with 3 μM Aβ42 or with TFD and the indicated Pen1-siRNA. Survival was quantified after 1 day for each point (n=3), and the experiment was replicated 5 times.

FIG. 5 depicts results of experiments indicating that PIDD null neurons are sensitive to Aβ or TFD and that active Caspase 2 is induced in PIDD-null neurons by TFD. Left: primary neurons from PIDD-null mice were treated with 3 μM Aβ42 or with TFD and the indicated Pen1-siRNA. Survival was quantified at 1 day. Right: Cultures were treated with 50 μM bVAD for 2 hrs and then TFD for 1 hr and bVAD-Caspase 2 complexes were analyzed by western blotting.

Figure 6A:
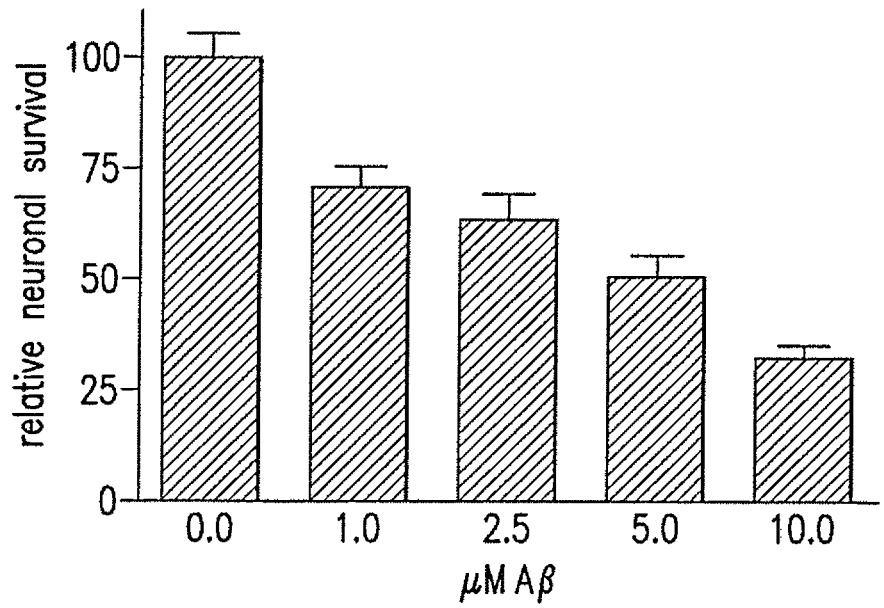
Figure 6B:
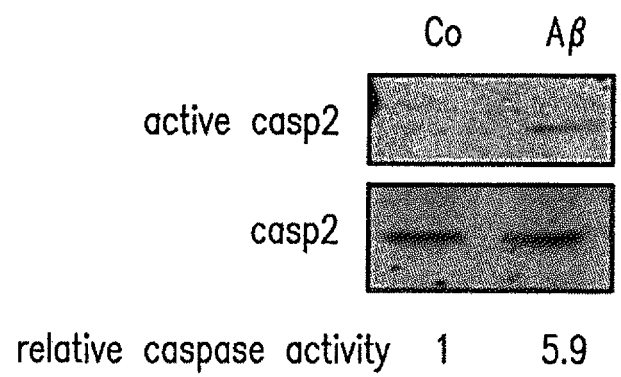

FIG. 6A-B depicts results of experiments indicating that Aβ induces Caspase 2 activity and neuronal death. A. Primary hippocampal neurons were treated with increasing concentrations of Aβ. Survival was quantified after 1 day, n=3. B. Primary hippocampal neurons were treated with 50 μM bVAD for 2 hrs and then with 3 μM Ab42 for 30 minutes. Cultures were harvested, bVAD-caspase complexes analyzed by Western blotting. Relative induction of active Caspase 2 is indicated below the blots. These are representative blots, n=2.

Figure 7:
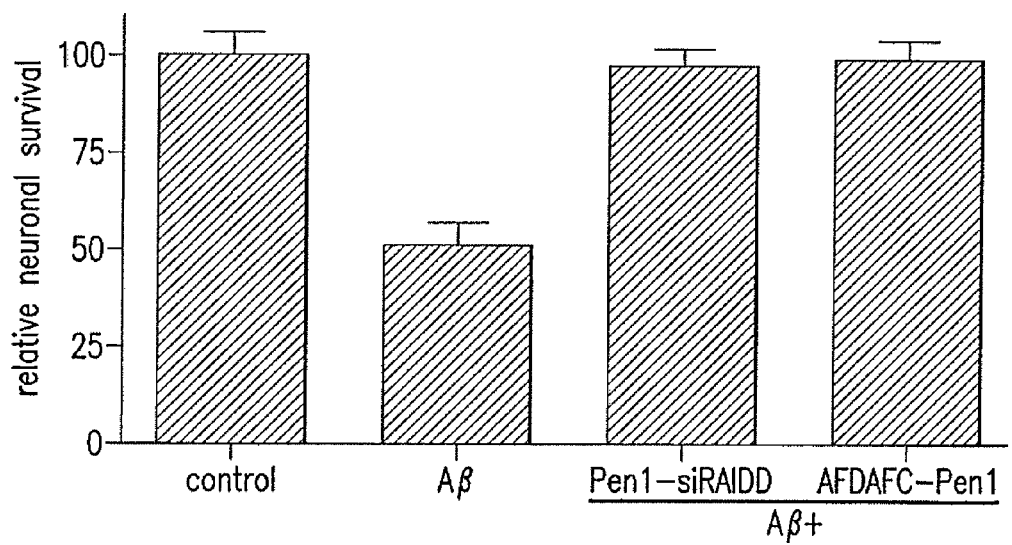

FIG. 7 depicts results of experiments indicating that the AFDAFC-Pen1 Caspase 2 activation inhibitor abrogates Aβ-mediated cell death. Primary hippocampal cells were treated with $Aβ_{1-42}$ and either Pen1-siRAIDD or AFDAFC-Pen1. Survival was quantified after 1 day, n=3.

Figure 8:
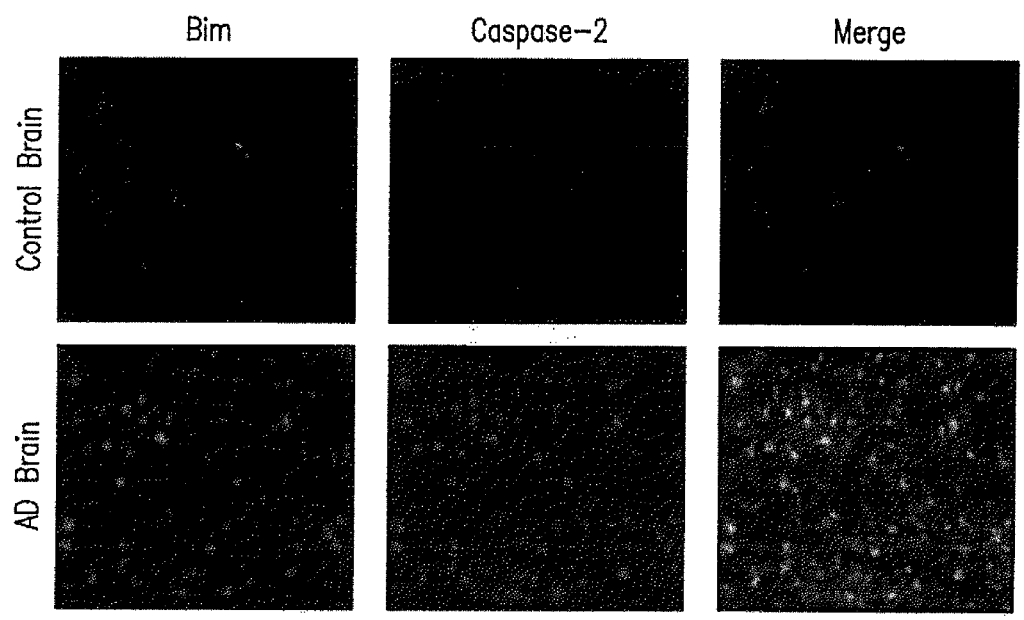

FIG. 8 Entorhinal cortical neurons of post-mortem AD brains with elevated Bim immunostaining also show elevated Caspase 2 immunostaining. Sections of entorhinal cortex from six AD and six age-matched controls were co-immunostained for Bim (red) and Caspase 2 (green). Representative images were taken for each case by using an inverted fluorescent microscope and camera set to the same exposure time. Images were taken at 20×. Representative images are shown illustrating the elevation and co-expression of Bim and Caspase 2.

FIGS. 9A-9D $Aβ_{1-42}$ and NGF deprivation promote rapid activation of Caspase 2 and $Aβ_{1-42}$ activates Caspase 2 before Bim induction. A. Specificity of anti-Caspase 2 antiserum in Western immunoblotting. Whole brain extracts from postnatal day 1 (P1) wild-type and Caspase 2 knockout mice were used to assess the specificity of the affinity purified rabbit polyclonal Caspase 2 antibody. B. $Aβ_{1-42}$ induces rapid activation of Caspase 2 in hippocampal neurons. Hippocampal neuron cultures were treated with 50 μM bVAD-fmk for 2 hours and then with or without 3 μM $Aβ_{1-42}$ for an additional 30 mins. Activated Caspase 2 was pulled-down with streptavidin beads and identified by Western immunoblot analysis using affinity purified polyclonal Caspase 2 antibody. The bar graph represents the mean values±SEM for densitometric analysis of activated Caspase 2 levels normalized to β-tubulin. Data are expressed as fold changes relative to control. * indicates that mean value is significantly different from control (p<0.05), by unpaired Student's t test (N=3). C. $A\beta_{1-42}$ treatment and NOF deprivation induce rapid activation of Caspase 2 in sympathetic neurons. Sympathetic neuron cultures were treated with 50 µM bVAD-fink for 2 hours prior to and then with or without 3 µM $A\beta_{1-42}$ treatment or NGF-deprivation (–NGF) for 2 hrs. Active Caspase 2 was pulled-down by streptavidin beads and identified by Western immunoblot analysis using polyclonal Caspase 2 antibody. Representative blots are shown; the experiments were replicated 3 times. Data normalization, fold change and statistical analyses performed as in B. *** indicates that the mean value is significantly different from control (p<0.0004). D. Elevation of Bim in response to $A\beta_{1-42}$ occurs later than Caspase 2 activation. Hippocampal neuron cultures were treated with or without 3 µM $A\beta_{1-42}$ for the indicated times and Bim levels were assessed by Western immunoblotting.

FIGS. 10A-10E Bim induction requires caspase activity. A. Pen-siBim effectively knocks down Bim expression. Hippocampal neuron cultures were treated with or without Pen1-siBim (80 nM) for 5 hours. Cultures were analyzed by Western blot for Bim protein expression; β-tubulin was used as a loading control. Bim knockdown is to 43% of control levels. B. Knockdown of Bim does not compromise activation of Caspase 2 by $A\beta_{1-42}$ treatment. Hippocampal neuron cultures were treated with bVAD-fink (50 µM) and with or without Pen1-siBim (80 nM) for 3 hours and then with or without 3 µM $A\beta_{1-42}$ for an additional 2 hours. Active Caspase 2 was pulled down using streptavidin beads and identified by Western blot analysis with a polyclonal Caspase 2 specific antibody. Representative blots are shown; the experiments were replicated 3 times. Data normalization, fold change and statistical analyses performed as in FIG. 8B. * indicates that the mean value is significantly different from control (p<0.0005), ns indicates that the 2 treatments are not significantly different from each other, by unpaired Student's t test (N=3). C. bVAD-fink pretreament blocks Bim mRNA induction by $A\beta_{1-42}$. Hippocampal neuron cultures were treated with 50 µM bVAD-fink for 2 hours prior to and then with or without 3 µM $A\beta_{1-42}$ for an additional 4 hours (bVAD-fink pre-treatment) or with 3 µM A1-42 for a total of 4 hrs with 50 µM bVAD-fink added during the last 2 hours of incubation (bVAD-fink post-treatment). Cultures were analyzed by qPCR for Bim expression. Bim mRNA levels were normalized to β-tubulin mRNA expression and are expressed as mean values±SEM.  indicates that mean value is significantly different from control (p<0.003). (N=3). D. bVAD-fmk pretreatment blocks Bim protein induction by $A\beta_{1-42}$. Hippocampal neuron cultures were treated as in C and analyzed by Western blot for Bim protein expression; β-tubulin was used as a loading control. A representative blot is shown; the experiment was replicated 3 times. Data normalization, fold change and statistical analyses performed as in FIG. 8B.  indicates that mean value is significantly different from control (p<0.007). E. bVAD-fmk pretreatment captures Caspase 2 activated by $A\beta_{1-42}$ treatment. Hippocampal neuron cultures were pre-treated with bVAD-fink as in FIG. 9B, Activated Caspase 2 was pulled down using streptavidin beads and identified by Western blot analysis with a polyclonal Caspase 2 specific antibody. A representative blot is shown; the experiments were replicated 3 times. Data normalization, fold change and statistical analyses performed as in FIG. 8B.  indicates that mean value is significantly different from control (p<0.005).

FIGS. 11A-11G Caspase 2 is required for induction of Bim protein levels by apoptotic stimuli in hippocampal neurons and sympathetic neurons. A. Pen-siCaspase 2 rapidly knocks down Caspase 2. Hippocampal neuron cultures were treated with or without Pen1-siCaspase 2 (80 nM) for the indicated times and analyzed by Western blot with a polyclonal Caspase 2 specific antibody; β-tubulin was used as a loading control. B. Knockdown of Caspase 2 inhibits induction of Bim mRNA by $A\beta_{1-42}$ in hippocampal cultures. Hippocampal neuron cultures were treated for 2 hours with Pen1-Caspase 2 (80 nM) and then treated with or without 3 µM $A\beta_{1-42}$ for 4 hours and analyzed by qPCR for Bim expression. Bim mRNA levels were normalized to β-tubulin mRNA.  indicates that mean value is significantly different from control (p<0.002), (N=3). C. Knockdown of Caspase 2 inhibits induction of Bim mRNA by $A\beta_{1-42}$ or NGF-deprivation in sympathetic neurons cultured from wild-type mice. Wild-type sympathetic neuron cultures were treated for 2 hours with Pen1-siCaspase 2 and then with or without 3 µM $A\beta_{1-42}$ or NGF deprivation for 4 hours. Culture extracts were analyzed by qPCR for Bim expression and Bim mRNA levels were normalized to β-tubulin mRNA expression and are expressed as mean values±SEM. * indicates that mean value is significantly different from control (p<0.0001), by unpaired Student's t test (N=3). D. Bim mRNA is not induced by $A\beta_{1-42}$ or NGF deprivation in sympathetic neuron cultured from Caspase 2 null mice. Caspase 2 null sympathetic neuron cultures were treated with or without 3 µM $A\beta_{1-42}$ or NGF deprivation for 4 hours and analyzed by qPCR for Bim mRNA expression. Relative Bim mRNA levels were normalized to β-tubulin mRNA expression and values given as means±SEM. There are no significant differences from control, (N=3). E. Knockdown of Caspase 2 inhibits induction of Bim protein in hippocampal neurons by $A\beta_{1-42}$. Hippocampal neurons were treated for 8 hrs with or without 3 µM $A\beta_{1-42}$ in the presence or absence of Pen1-siCaspase 2 (80 nM). Bim levels were determined by Western blotting with normalization to ERK. A representative blot is shown. The bar graph shows the densitometric analysis of Bim levels normalized to ERK under each condition. All data are expressed as mean fold changes relative to control±SEM. * indicates that mean value is significantly different from control (p<0.05);  indicates that mean value is significantly different from $A\beta_{1-42}$ (p<0.05) by ANOVA, Bonferroni post-hoc test (N=7). F. $A\beta_{1-42}$ induced Bim up-regulation is not affected by a non-related siRNA. Hippocampal neurons were treated for 2 hrs with or without 3 µM $A\beta_{1-42}$ and with or without Pen1-siLuciferase (80 nM). Bim levels were determined by Western blotting. G. Apoptotic stimuli induce Bim expression in sympathetic neurons cultured from wild-type, but not Caspase 2 null mice. Sympathetic neurons from P1 wild-type and Caspase 2 null mice were treated for 6 hrs with or without 3 µM $A\beta_{1-42}$ or subjected to NGF-deprivation for 6 hrs. Wild-type cultures were also pretreated with Pen1-siCaspase 2 for 2 hrs as indicated. Bim was visualized by immunocytochemistry using a PerkinElmer spinning disc confocal, 60× magnification and cultures were blindly scored as previously described (Biswas et al., J Neurosci. 27:893-900, 2007) for proportions of neurons with high Bim staining. Left-hand panels show photos of representative cultures under indicated conditions. Right hand panels show quantification of proportions of neurons with high Bim expression under each condition. Values are means±SEM.  indicates that mean value is significantly different from control (p<0.0015), by unpaired Student's t test (N=3).

Figure 12A:
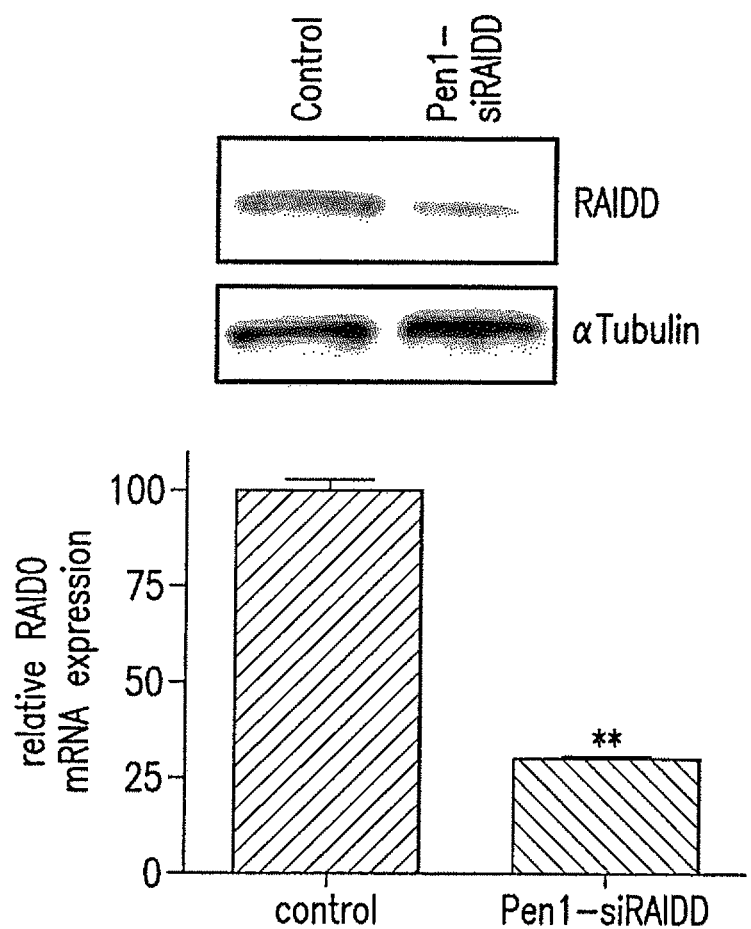
Figure 12B:
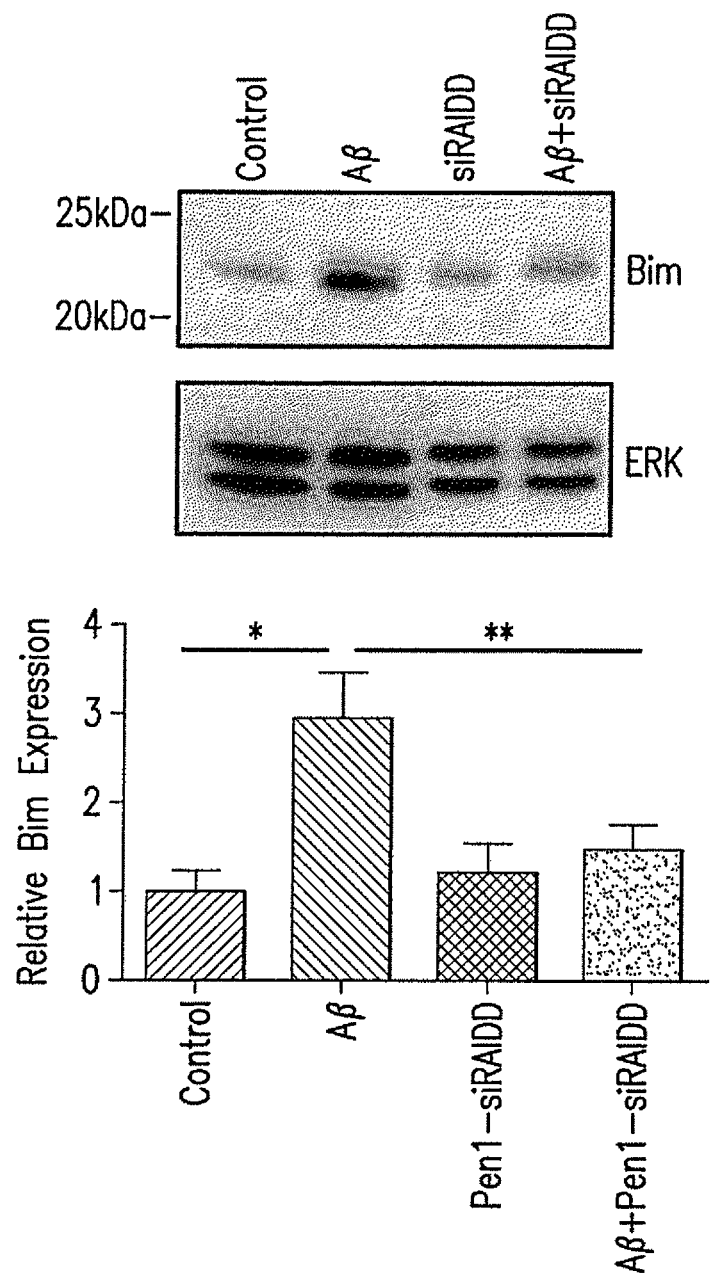

FIGS. 12A-12B RAIDD is required for Bim protein induction in hippocampal neurons by $A\beta_{1-42}$. A. Pen1-siRAIDD knocks down RAIDD expression. Hippocampal neuron cultures were treated for 4 hrs with Pen1-siRAIDD (80 nM). RAIDD protein and mRNA levels were assessed by Western immunoblotting (left) and qPCR (right), respectively.

RAIDD mRNA levels were normalized to β-tubulin mRNA expression. ** indicates that mean value is significantly different from control (p<0.0015), (N=3). B. Knockdown of RAIDD blocks Bim protein induction by $A\beta_{1-42}$. Hippocampal neuron cultures were treated for 8 hrs with or without 3 μM $A\beta_{1-42}$ in the presence or absence of Pen1-siRAIDD (80 nM). Bim levels were assessed by Western blotting. A representative blot is shown. * indicates that mean value is significantly different from control (p<0.05); ** indicates that mean value is significantly different from $A\beta_{1-42}$ (p<0.05) by ANOVA, Bonferroni post-hoc test (N=6).

Figure 13:
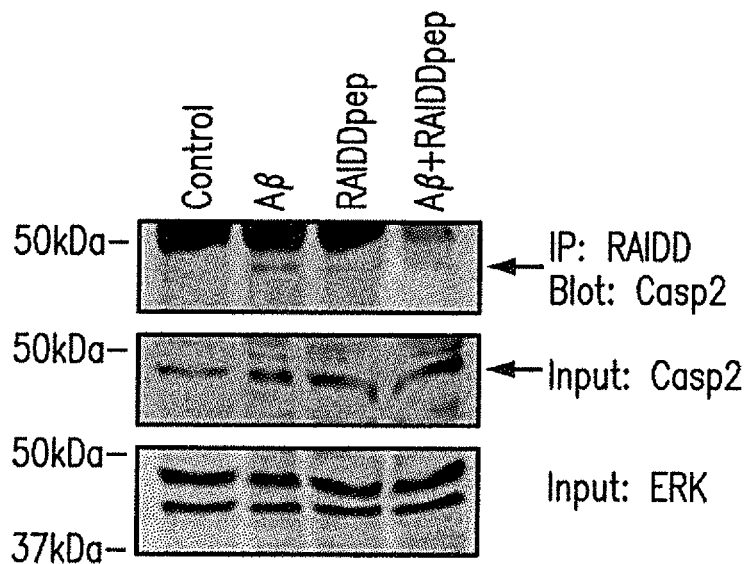

FIG. 13 AFDAFC-Pen1 reduces $A\beta_{1-42}$-induced binding of Caspase 2 to RAIDD. Western blot showing levels of Caspase. 2 bound to endogenous RAIDD in control conditions, in the presence of $A\beta_{1-42}$, in the presence of AFDAFC-Pen1, and in the presence of $A\beta_{1-42}$ and AFDAFC-Pen1 in primary hippocampal neurons. The level of Caspase 2 bound to endogenous RAIDD increased in $A\beta_{1-42}$-treated cells. This increase was not seen in cells treated with AFDAFC-Pen1 prior to $A\beta_{1-42}$ treatment.

Figure 14:
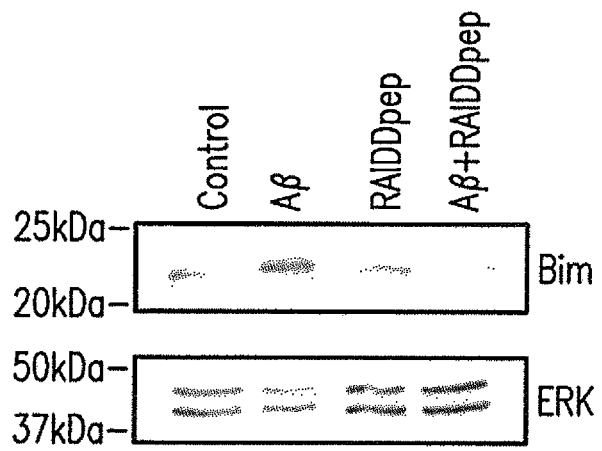

FIG. 14 AFDAFC-Pen1 prevents Bim induction elicited by $A\beta_{1-42}$. Western blot showing levels of Bim in control conditions, in the presence of $A\beta_{1-42}$, in the presence of AFDAFC-Peril, and in the presence of $A\beta_{1-42}$ and AFDAFC-Pen1 in primary hippocampal neurons. The level of Bim increased in cells treated with $A\beta_{1-42}$. This increase was not seen in cells treated with AFDAFC-Pen1 prior to $A\beta_{1-42}$.

Figure 15A:
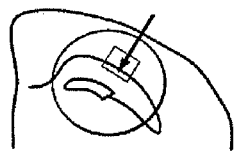
Figure 15B:
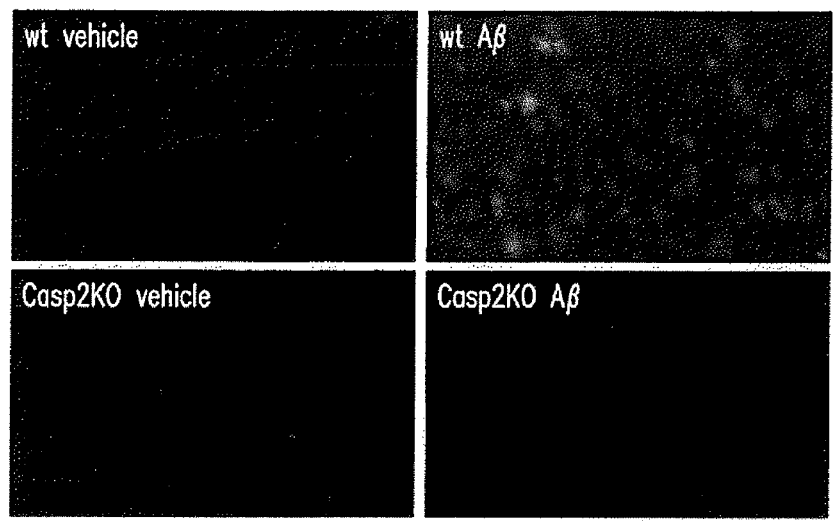
Figure 15C:
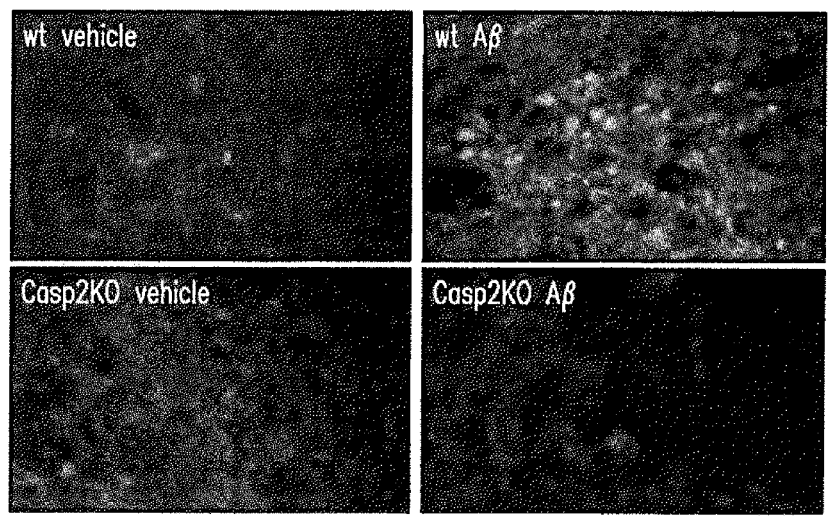

FIGS. 15A-C Both Caspase 2 and RAIDD are required for cJun phosphorylation and nuclear localization in hippocampal neurons by $A\beta_{1-42}$. A. Caspase 2 is required for elevation of cJun phosphorylation in response to $A\beta_{1-42}$. Hippocampal neurons were treated for 8 hrs with or without 3 μM $A\beta_{1-42}$ in the presence or absence of Pen1-siCaspase 2 (80 nM). Phospho-cJun (Ser 63) levels were assessed by Western immunoblotting. Blots from a representative experiment are shown. The bar graphs represent the results from densitometric analysis of Phospho-cJun (Ser 63) levels normalized to β-tubulin. * indicates that mean value is significantly different from control (p<0.05); ** indicates that mean value is significantly different from $A\beta_{1-42}$ (p<0.05) by ANOVA, Bonferroni post-hoc test (N=5). B. RAIDD is required for elevation of atm phosphorylation in response to $A\beta_{1-42}$. Hippocampal neurons were treated for 8 hrs with or without 3 μM $A\beta_{1-42}$ in the presence or absence of Pen1-siRAIDD (80 nM). Phospho-cJUN (Ser 63) levels were assessed by Western immunoblotting. Blots from a representative experiment are shown. The bar graphs represent results from densitometric analysis of Phospho-cJun (Ser 63) levels normalized to β-tubulin. * indicates that mean value is significantly different from control (p<0.05);  indicates that mean value is significantly different from $A\beta_{1-42}$ (p<0.05) by ANOVA, Bonferroni post-hoc test (N=4). C. Both Caspase 2 and RAIDD are required for elevated nuclear localization of phospho-Jun in hippocampal neurons in response to $A\beta_{1-42}$ treatment. Hippocampal neurons were treated for 8 hrs with or without 3 μM $A\beta_{1-42}$ in the presence or absence of Pen1-siCaspase 2 or Pen1-siRAIDD (80 nM). Phospho-cJun (Ser 63) was visualized by immunocytochemistry using PerkinElmer spinning disc confocal, 60× magnification. Representative images are shown for each condition. Blinded counts were carried out to assess the proportions of neurons under each condition with strong nuclear staining of Phospho-cJun (Ser 63). * indicates that mean value is significantly different from control (p<0.0008); *** indicates that mean value is significantly different from A1-42 (p<0.001) by ANOVA, Bonferroni post-hoc test (N=3).

Figure 16A:
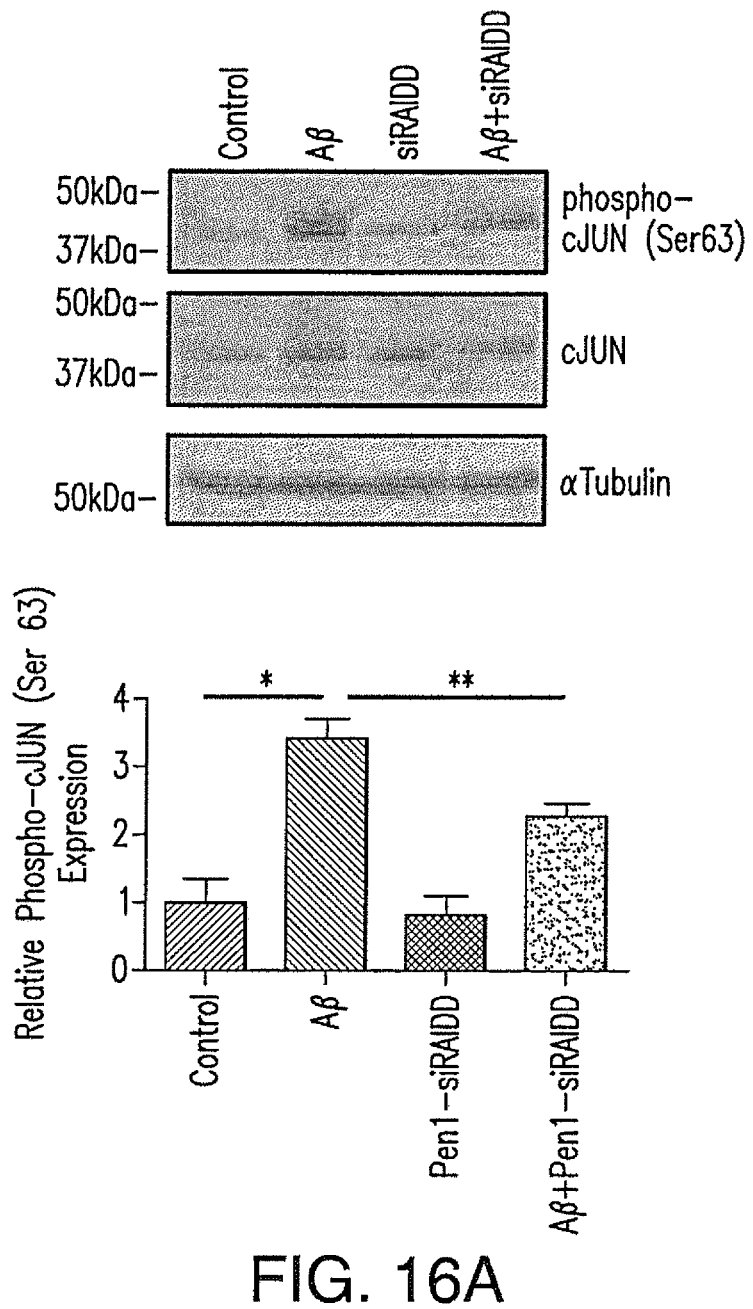
Figure 16B:
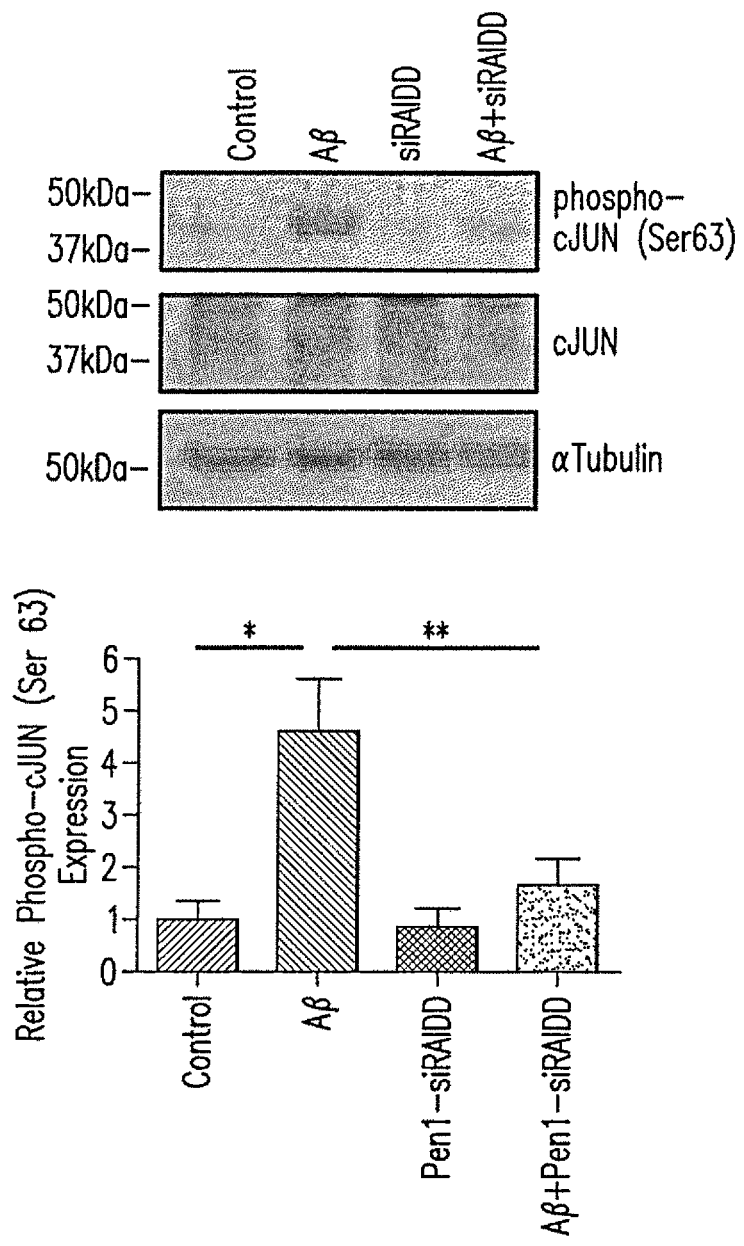
Figure 16C:
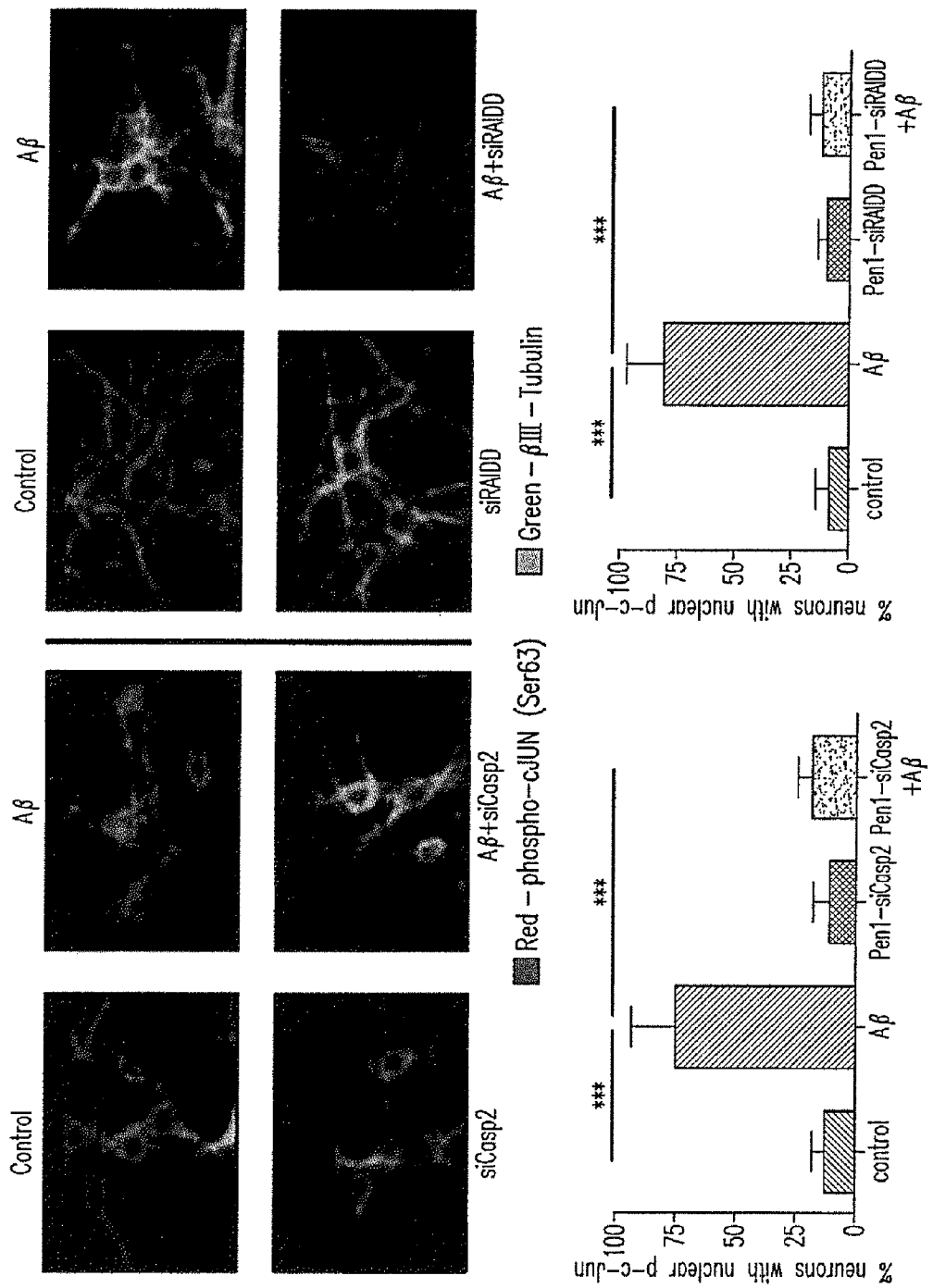

FIGS. 16A-16C Caspase 2 is required for Bim induction in an in vivo model of AD pathology. $A\beta_{1-42}$ (0.4 moles) or vehicle was infused into the right hippocampi of 16-month-old wild-type (n=8 mice, 4 vehicle, 4 $A\beta_{1-42}$) and Caspase 2 null mice (n=8, 4 vehicle, 4 $A\beta_{1-42}$). 2 weeks later the animals were sacrificed and the brains processed for immunohistochemistry. A. Schematic indicating where $A\beta_{1-42}$ was delivered (red arrow indicates site of delivery) and approximate spread, based on staining with an antibody specific for oligomerized $A\beta_{1-42}$, of $A\beta_{1-42}$ in the brain. The green rectangle indicates the area imaged for B and C. B. Bim immunostaining. Coronal sections from each cohort of animals were immunostained for Bim and imaged with a PerkinElmer spinning disc confocal microscope, 40× magnification. 4 animals were treated per condition, representative images are shown. C. Fluoro-jade B staining. Sections adjacent to those used for B were stained with Fluoro jade B and imaged with a PerkinElmer spinning disc confocal microscope, 40× magnification. 4 animals were treated per condition, representative images are shown.

5. DETAILED DESCRIPTION OF THE INVENTION 5.1 Caspase 2 Activation Inhibitor Compositions
5.1.1 Caspase 2 Activation Inhibitory Peptide In certain embodiments, the instant invention relates to a Caspase 2 activation inhibitory peptide having the amino acid sequence AFDAFC (SEQ ID NO: 1).

In certain embodiments, the Caspase 2 activation inhibitors of the present invention include those amino acid sequences that retain certain structural and functional features of the Caspase 2 activation inhibitory peptide having the amino acid sequence AFDAFC (SEQ ID NO: 1), yet differ from that inhibitor's amino acid sequence at one or more positions. Such polypeptide variants can be prepared by substituting, deleting, or adding amino acid residues from the original sequence via methods known in the art.

In certain embodiments, such substantially similar sequences include sequences that incorporate conservative amino acid substitutions. As used herein, a "conservative amino acid substitution" is intended to include a substitution in which the amino acid residue is replaced with an amino acid residue having a similar side chain. Families of amino acid residues having similar side chains have been defined in the art, including: basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine); nonpolar side chains (e.g., alanine, valine, leucine, isoleucine, praline, phenylalanine, methionine, tryptophan); β-branched side chains (e.g., threonine, valine, isoleucine); and aromatic side chains (e.g., tyrosine, phenylalanine, tryptophan, histidine). Other generally preferred substitutions involve replacement of an amino acid residue with another residue having a small side chain, such as alanine or glycine. Amino acid substituted peptides can be prepared by standard techniques, such as automated chemical synthesis.

In certain embodiments, a polypeptide of the present invention is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% homologous to the AFDAFC (SEQ ID NO: 1) amino acid sequence of the Caspase 2 activation inhibitory peptide and is capable of Caspase 2 activation inhibition. As used herein, the percent homology between two amino acid sequences may be determined using standard software such as BLAST or FASTA. The effect of the amino acid substitutions on the ability of the synthesized polypeptide to inhibit Caspase 2 activation can be tested using the methods disclosed in Examples section, below.

In certain non-limiting embodiments, the invention relates to a Caspase 2 inhibitory peptide comprising the amino acid sequence AFDAFC (SEQ ID NO: 1) and additional amino acids linked to either or both the N-terminal or C-terminal end of said sequence, for example, one, two, three, four, five or six amino acids linked to the N-terminal and/or C-terminal end of AFDAFC (SEQ ID NO: 1).

5.1.2 Caspase 2 Activation Inhibitor-Cell Penetrating Peptide Conjugates

In certain embodiments of the instant invention, the Caspase 2 activation inhibitory peptide is conjugated to a cell penetrating peptide to form a Caspase 2 activation inhibitor-cell penetrating peptide conjugate. The conjugate can facilitate delivery of the inhibitor into a cell associated with a neurodegenerative condition, including, but not limited to those conditions associated with apoptosis in the central nervous system. Such conditions include, but are not limited to, Alzheimer's Disease, Mild Cognitive Impairment, Parkinson's Disease, amyotrophic lateral sclerosis, Huntington's chorea, and Creutzfeld-Jacob disease.

As used herein, a "cell-penetrating peptide" is a peptide that comprises a short (about 9-30 residues) amino acid sequence or functional motif that confers the energy-independent (i.e., non-endocytotic) translocation properties associated with transport of the membrane-permeable complex across the plasma and/or nuclear membranes of a cell. In certain embodiments, the cell-penetrating peptide used in the membrane-permeable complex of the present invention preferably comprises at least one non-functional cysteine residue, which is either free or derivatized to form a disulfide link with the Caspase 2 activation inhibitor, which has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, Peril, transportan, pIs1, TAT(48-60), pVEC, MTS, and MAP.

The cell-penetrating peptides of the present invention include those sequences that retain certain structural and functional features of the identified cell-penetrating peptides, yet differ from the identified peptides' amino acid sequences at one or more positions. Such polypeptide variants can be prepared by substituting, deleting, or adding amino acid residues from the original sequences via methods known in the art.

In certain embodiments, such substantially similar sequences include sequences that incorporate conservative amino acid substitutions, as described above in connection with the Caspase 2 activation inhibitor. In certain embodiments, a cell-penetrating peptide of the present invention is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% homologous to the amino acid sequence of the identified peptide and is capable of mediating cell penetration. The effect of the amino acid substitutions on the ability of the synthesized peptide to mediate cell penetration can be tested using the methods disclosed in Examples section, below.

In certain embodiments of the present invention, the cell-penetrating peptide of the membrane-permeable complex is penetratin1, comprising the peptide sequence RQIKIWFQN-RRMKWKK (SEQ ID NO: 2), or a conservative variant thereof. As used herein, a "conservative variant" is a peptide having one or more amino acid substitutions, wherein the substitutions do not adversely affect the shape—or, therefore, the biological activity (i.e., transport activity) or membrane toxicity—of the cell-penetrating peptide.

Pen1 is a 16-amino-acid polypeptide derived from the third alpha-helix of the homeodomain of *Drosophila antennapedia*. Its structure and function have been well studied and characterized: Derossi et al., Trends Cell Biol., 8(2):84-87, 1998; Dunican et al., Biopolymers, 60(1):45-60, 2001; Hallbrink et al., Biochim. Biophys. Acta, 1515(2):101-09, 2001; Bolton et al., Eur. J. Neurosci., 12(8):2847-55, 2000; Kilk et al., Bioconjug. Chem., 12(6):911-16, 2001; Bellet-Amalric et al., Biochim. Biophys. Acta, 1467(1):131-43, 2000; Fischer et al., J. Pept. Res., 55(2): 163-72, 2000; Thoren et al., FEBS Lett., 482(3):265-68, 2000.

It has been shown that Pen1 efficiently carries avidin, a 63-kDa protein, into human Bowes melanoma cells (Kilk et al., Bioconjug. Chem., 12(6):911-16, 2001). Additionally, it has been shown that the transportation of penetratin1 and its cargo is non-endocytic and energy-independent, and does not depend upon receptor molecules or transporter molecules. Furthermore, it is known that penetratin1 is able to cross a pure lipid bilayer (Thoren et al., FEBS Lett., 482(3): 265-68, 2000). This feature enables Pen1 to transport its cargo, free from the limitation of cell-surface-receptor/-transporter availability. The delivery vector previously has been shown to enter all cell types (Derossi et al., Trends Cell Biol., 8(2):84-87, 1998), and effectively to deliver peptides (Troy et al., Proc. Natl. Acad. Sci. USA, 93:5635-40, 1996) or antisense oligonucleotides (Troy et al., J. Neurosci., 16:253-61, 1996; Troy et al., J. Neurosci., 17:1911-18, 1997).

Other non-limiting embodiments of the present invention involve the use of the following exemplary cell permeant molecules: RL16 (H-RRLRRLLRRLLRRLRR-OH) (SEQ ID NO: 3), a sequence derived from Pen1 with slightly different physical properties (Biochim Biophys Acta. 2008 July-August; 1780(7-8):948-59); and RVGRRRRRRRRR (SEQ ID NO: 4), a rabies virus sequence which targets neurons see P. Kumar, H. Wu, J. L. McBride, K. E. Jung, M. H. Kim, B. L. Davidson, S. K. Lee, P. Shankar and N. Manjunath, Transvascular delivery of small interfering RNA to the central nervous system, *Nature* 448 (2007), pp. 39-43.

In certain alternative non-limiting embodiments of the present invention, the cell-penetrating peptide of the membrane-permeable complex is a cell-penetrating peptides selected from the group consisting of: transportan, pIS1, Tat (48-60), pVEC, MAP, and MTS. Transportan is a 27-amino-acid long peptide containing 12 functional amino acids from the amino terminus of the neuropeptide galanin, and the 14-residue sequence of mastoparan in the carboxyl terminus, connected by a lysine (Pooga et al., FASEB J., 12(1):67-77, 1998). It comprises the amino acid sequence GWTLN-SAGYLLGKINLKALAALAKKIL (SEQ ID NO: 5), or a conservative variant thereof.

pIs1 is derived from the third helix of the homeodomain of the rat insulin 1 gene enhancer protein (Magzoub et al., Biochim. Biophys. Acta, 1512(1):77-89, 2001; Kilk et al., Bioconjug. Chem., 12(6):911-16, 2001). pIs1 comprises the amino acid sequence PVIRVW FQNKRCKDKK (SEQ ID NO: 6), or a conservative variant thereof.

Tat is a transcription activating factor, of 86-102 amino acids, that allows translocation across the plasma membrane of an HIV-infected cell, to transactivate the viral genome (Hallbrink et al., Biochem. Biophys. Acta., 1515(2):101-09, 2001; Suzuki et al., J. Biol. Chem., 277(4):2437-43, 2002; Futaki et al., J. Biol. Chem., 276(8):5836-40, 2001). A small Tat fragment, extending from residues 48-60, has been determined to be responsible for nuclear import (Vives et al., J. Biol. Chem., 272(25):16010-017, 1997); it comprises the amino acid sequence RKKRRQRRR (SEQ ID NO: 7), or a conservative variant thereof.

pVEC is an 18-amino-acid-long peptide derived from the murine sequence of the cell-adhesion molecule, vascular endothelial cadherin, extending from amino acid 615-632 (Elmquist et al., Exp. Cell Res., 269(2):237-44, 2001). pVEC comprises the amino acid sequence LLIILRRRIRKQAHAH (SEQ ID NO: 8), or a conservative variant thereof.

MTSs, or membrane translocating sequences, are those portions of certain peptides which are recognized by the acceptor proteins that are responsible for directing nascent translation products into the appropriate cellular organelles for further processing (Lindgren et al., Trends in Pharmacological Sciences, 21(3):99-103, 2000; Brodsky, J. L., Int. Rev. Cyt., 178:277-328, 1998; Zhao et al., J. Immunol. Methods, 254(1-2):137-45, 2001). An MTS of particular relevance is MPS peptide, a chimera of the hydrophobic terminal domain of the viral gp41 protein and the nuclear localization signal from simian virus 40 large antigen; it represents one combination of a nuclear localization signal and a membrane translocation sequence that is internalized independent of temperature, and functions as a carrier for oligonucleotides (Lindgren et al., Trends in Pharmacological Sciences, 21(3): 99-103, 2000; Morris et al., Nucleic Acids Res., 25:2730-36, 1997). MPS comprises the amino acid sequence GALFLG-WLGAAGSTMGAWSQPKKKRKV (SEQ ID NO: 9), or a conservative variant thereof.

Model amphipathic peptides, or MAPs, form a group of peptides that have, as their essential features, helical amphipathicity and a length of at least four complete helical turns (Scheller et al., J. Peptide Science, 5(4):185-94, 1999; Hallbrink et al., Biochim. Biophys. Acta., 1515(2):101-09, 2001). An exemplary MAP comprises the amino acid sequence KLALKLALKALKAALKLA-amide (SEQ ID NO: 10), or a conservative variant thereof.

In certain embodiments, a cell-penetrating peptide and the Caspase 2 activation inhibitor described above are covalently bound to form a conjugate. In certain embodiments the cell penetrating peptide is linked to the Caspase 2 inhibitor via an amide bond. In certain embodiments the cell-penetrating peptide is operably linked to a peptide Caspase 2 activation inhibitor via recombinant DNA technology. For example, a nucleic acid sequence encoding that Caspase 2 activation inhibitor can be introduced either upstream (for linkage to the amino terminus of the cell-penetrating peptide) or downstream (for linkage to the carboxy terminus of the cell-penetrating peptide), or both, of a nucleic acid sequence encoding the Caspase 2 activation inhibitor of interest. Such fusion sequences comprising both the Caspase 2 activation inhibitor encoding nucleic acid sequence and the cell-penetrating peptide encoding nucleic acid sequence can be expressed using techniques well known in the art.

In certain embodiments, the Caspase 2 activation inhibitor can be operably linked to the cell-penetrating peptide via a non-covalent linkage. In certain embodiments such non-covalent linkage is mediated by ionic interactions, hydrophobic interactions, hydrogen bonds, or van der Waals forces.

In certain embodiments, the Caspase 2 activation inhibitory peptide is operably linked to the cell penetrating peptide via a chemical linker. Examples of such linkages typically incorporate 1-30 nonhydrogen atoms selected from the group consisting of C, N, O, S and P. Exemplary linkers include, but are not limited to, a substituted alkyl or a substituted cycloalkyl. Alternately, the heterologous moiety may be directly attached (where the linker is a single bond) to the amino or carboxy terminus of the cell-penetrating peptide. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. In certain embodiments, the linker incorporates less than 20 nonhydrogen atoms and are composed of any combination of ether, thioether, urea, thiourea, amine, ester, carboxamide, sulfonamide, hydrazide bonds and aromatic or heteroaromatic bonds. In certain embodiments, the linker is a combination of single carbon-carbon bonds and carboxamide, sulfonamide or thioether bonds.

A general strategy for conjugation involves preparing the cell-penetrating peptide and the Caspase 2 activation inhibitory peptide components separately, wherein each is modified or derivatized with appropriate reactive groups to allow for linkage between the two. The modified Caspase 2 activation inhibitory peptide is then incubated together with a cell-penetrating peptide that is prepared for linkage, for a sufficient time (and under such appropriate conditions of temperature, pH, molar ratio, etc.) as to generate a covalent bond between the cell-penetrating peptide and the Caspase 2 activation inhibitory peptide molecule.

Numerous methods and strategies of conjugation will be readily apparent to one of ordinary skill in the art, as will the conditions required for efficient conjugation. By way of example only, one such strategy for conjugation is described below, although other techniques, such as the production of fusion proteins or the use of chemical linkers is within the scope of the instant invention.

In certain embodiments, when generating a disulfide bond between Caspase 2 activation inhibitory peptide molecule and the cell-penetrating peptide of the present invention, the thiol present on the terminal cysteine of the Caspase 2 activation inhibitory peptide molecule is employed and a nitropyridyl leaving group can be manufactured on a cysteine residue of the cell-penetrating peptide. Any suitable bond (e.g., thioester bonds, thioether bonds, carbamate bonds, etc.) can be created according to methods generally and well known in the art. Both the derivatized or modified cell-penetrating peptide, and the thiol-containing Caspase 2 activation inhibitory peptide are reconstituted in RNase/DNase sterile water, and then added to each other in amounts appropriate for conjugation (e.g., equimolar amounts). The conjugation mixture is then incubated for 15 min at 65° C., followed by 60 min at 37° C., and then stored at 4° C. Linkage can be checked by running the vector-linked Caspase 2 activation inhibitory peptide molecule, and an aliquot that has been reduced with DTT, on a 15% non-denaturing PAGE. Caspase 2 activation inhibitory peptide molecules can then be visualized with the appropriate stain.

5.1.3 Pharmaceutical Compositions

In certain embodiments, the Caspase 2 activation inhibitory peptide, or membrane-permeable complexes thereof, are formulated for nasal administration. For nasal administration, solutions or suspensions comprising the Caspase 2 activation inhibitory peptide, or membrane-permeable complexes thereof, can be formulated for direct application to the nasal cavity by conventional means, for example with a dropper, pipette or spray. Other means for delivering the nasal spray composition, such as inhalation via a metered dose inhaler (MDI), may also be used according to the present invention. Several types of MDIs are regularly used for administration by inhalation. These types of devices can include breath-actuated MDI, dry powder inhaler (DPI), spacer/holding chambers in combination with MDI, and nebulizers. The term "MDI" as used herein refers to an inhalation delivery system comprising, for example, a canister containing an active agent dissolved or suspended in a propellant optionally with one or more excipients, a metered dose valve, an actuator, and a mouthpiece. The canister is usually filled with a solution or suspension of an active agent, such as the nasal spray composition, and a propellant, such as one or more hydrofluoroalkanes. When the actuator is depressed a metered dose of the solution is aerosolized for inhalation. Particles comprising the active agent are propelled toward the mouthpiece where they may then be inhaled by a subject. The formulations may be provided in single or multidose form. For example, in the case of a dropper or pipette, this may be achieved by the patient administering an appropriate, predetermined volume of the solution or suspension. In the case of a spray, this may be achieved for example by means of a metering atomising spray pump. To improve nasal delivery and retention the components according to the invention may be encapsulated with cyclodextrins, or formulated with agents expected to enhance delivery and retention in the nasal mucosa.

Commercially available administration devices that are used or can be adapted for nasal administration of a composition of the invention include the AERONEB™ (Aerogen, San Francisco, Calif.), AERONEB GO™ (Aerogen); PARI LC PLUS™, PART BOY™ N, PARI™ eflow (a nebulizer disclosed in U.S. Pat. No. 6,962,151), PART LC SINUS™, PARI SINUSTAR™., PART SINUNEB™, VibrENT™ and PART DURANEB™ (PARI Respiratory Equipment, Inc., Monterey, Calif. or Munich, Germany); MICROAIR™ (Omron Healthcare, Inc, Vernon Hills, Ill.), HALOLITE™ (Profile Therapeutics Inc, Boston, Mass.), RESPIMAT™ (Boehringer Ingelheim, Germany), AERODOSE™ (Aerogen, Inc, Mountain View, Calif.), OMRON ELITE™ (Omron Healthcare, Inc, Vernon Hills, Ill.), OMRON MICROAIR™ (Omron Healthcare, Inc, Vernon Hills, MABISMIST™ II (Mabis Healthcare, Inc, Lake Forest, Ill.), LUMISCOPE™ 6610, (The Lumiscope Company, Inc, East Brunswick, N.J.), AIRSEP MYSTIQUE™, (AirSep Corporation, Buffalo, N.Y.), ACORN-1™ and ACORN-II™ (Vital Signs, Inc, Totowa, N.J.), AQUATOWER™ (Medical Industries America, Adel., Iowa), AVA-NEB™ (Hudson Respiratory Care Incorporated, Temecula, Calif.), AEROCURRENT™ utilizing the AEROCELL™ disposable cartridge (AerovectRx Corporation, Atlanta, Ga.), CIRRUS™ (Intersurgical Incorporated, Liverpool, N.Y.), DART™ (Professional Medical Products, Greenwood, S.C.), DEVILBISS™ PULMO AIDE (DeVilbiss Corp; Somerset, Pa.), DOWNDRAFT™ (Marquest, Englewood, Colo.), FAN JET™ (Marquest, Englewood, Colo.), MB-5™ (Mefar, Bovezzo, Italy), MISTY NEB™ (Baxter, Valencia, Calif.), SALTER 8900™ (Salter Labs, Arvin, Calif.), SIDESTREAM™ (Medic-Aid, Sussex, UK), UPDRAFT-II™ (Hudson Respiratory Care; Temecula, Calif.), WHISPER JET™ (Marquest Medical Products, Englewood, Colo.), AIOLOS™ (Aiolos Medicnnsk Teknik, Karlstad, Sweden), INSPIRON™ (Intertech Resources, Inc., Bannockburn, Ill.), OPTIMIST™ (Unomedical Inc., McAllen, Tex.), PRODOMO™, SPIRA™ (Respiratory Care Center, Hameenlinna, Finland), AERx™ Essence™ and Ultra™, (Aradigm Corporation, Hayward, Calif.), SONIK™ LDI Nebulizer (Evit Labs, Sacramento, Calif.), ACCUSPRAY™ (BD Medical, Franklin Lake, N.J.), ViaNase ID™ (electronic atomizer; Kurve, Bothell, Wash.), OptiMist™ device or OPTINOSE™ (Oslo, Norway), MAD Nasal™ (Wolfe Tory Medical, Inc., Salt Lake City, Utah), Freepod™ (Valois, Marty le Roi, France), Dolphin™ (Valois), Monopowder™ (Valois), Equadel™ (Valois), VP3™ and VP7™ (Valois), VP6 Pump™ (Valois), Standard Systems Pumps™ (Ing. Erich Pfeiffer, Radolfzell, Germany), AmPump™ (Ing. Erich Pfeiffer), Counting Pump™ (Ing. Erich Pfeiffer), Advanced Preservative Free System™ (Ing. Erich Pfeiffer), Unit Dose System™ (Ing. Erich Pfeiffer), Bidose System™ (Ing. Erich Pfeiffer), Bidose Powder System™ (Ing. Erich Pfeiffer), Sinus Science™ (Aerosol Science Laboratories, Inc., Camarillo, Calif.), ChiSys™ (Archimedes, Reading, UK), Fit-Lizer™ (Bioactis, Ltd, a SNBL subsidiary (Tokyo, J P), Swordfish V™ (Mystic Pharmaceuticals, Austin, Tex.), DirectHaler™ Nasal (DirectHaler, Copenhagen, Denmark) and SWIRLER™ Radioaerosol System (AMICI, Inc., Spring City, Pa.).

To facilitate delivery to a cell, tissue, or subject, the Caspase 2 activation inhibitory peptide, or membrane-permeable complex thereof, may, in various compositions, be formulated with a pharmaceutically-acceptable carrier, excipient, or diluent. The term "pharmaceutically-acceptable", as used herein, means that the carrier, excipient, or diluent of choice does not adversely affect either the biological activity of the Caspase 2 activation inhibitory peptide, or membrane-permeable complex thereof, or the biological activity of the recipient of the composition. Suitable pharmaceutical carriers, excipients, and/or diluents for use in the present invention include, but are not limited to, lactose, sucrose, starch powder, talc powder, cellulose esters of alkonoic acids, magnesium stearate, magnesium oxide, crystalline cellulose, methyl cellulose, carboxymethyl cellulose, gelatin, glycerin, sodium alginate, gum arabic, acacia gum, sodium and calcium salts of phosphoric and sulfuric acids, polyvinylpyrrolidone and/or polyvinyl alcohol, saline, and water. Specific formulations of compounds for therapeutic treatment are discussed in Hoover, J. E., Remington's Pharmaceutical Sciences (Easton, Pa.: Mack Publishing Co., 1975) and Liberman and Lachman, eds., Pharmaceutical Dosage Forms (New York, N.Y.: Marcel Decker Publishers, 1980).

In accordance with the methods of the present invention, the quantity of the Caspase 2 activation inhibitory peptide, or membrane-permeable complex thereof, that is administered to a cell, tissue, or subject should be an amount that is effective to inhibit the Caspase 2 activation within the tissue or subject. This amount is readily determined by the practitioner skilled in the art. The specific dosage employed in connection with any particular embodiment of the present invention will depend upon a number of factors, including, but not limited to, the cell type expressing the target. Quantities will be adjusted for the body weight of the subject, and the particular disease or condition being targeted.

5.2 Methods of Treatment

Widespread neuron death occurs during normal development, after trauma, and in neurodegenerative diseases. Caspases, cysteine aspartate proteases, are known to be key mediators of such neuronal apoptotic death (Troy et al., Prog Mol Biol Trans' Sci. 99:265-305, 2011). In vertebrates, Caspase 2 is the most highly evolutionarily conserved member of the caspase family and the closest in sequence to *C. elegans* ced-3 (Lamkanfi et al., Cell Death Differ. 9:358-61, 2002). Yet, until the results outlined herein were obtained, there had been much uncertainty about the extent to which Caspase 2 participates in apoptotic death, the mechanism by which it does so and its hierarchical position in apoptotic cascades (Bouchier-Hayes and Green, Cell Death Differ. 19:51-7, 2012; Troy and Ribe, J Alzheimers Dis. 19:885-94, 2008).

The mitochondrion has been identified as a central element in apoptotic death mechanisms and an intrinsic "canonical pathway" has been described that leads to caspase activation (Tait and Green, Nat Rev Mol Cell Biol. 11:621-32, 2010). In this cascade, BH3-only members of the Bcl2 family promote the formation of BAK/BAX pores in the outer mitochondrial membrane through which apoptosis-stimulating proteins are released. Among these is cytochrome-c which, along with APAF1, activates caspase-9, an initiator caspase that in turn cleaves and activates death effector caspases including caspases-3, -6 and -7. In neurons and other cell types, a key initiating response to apoptotic signals that sets this cascade in motion is the transcription-dependent induction of BH3-only proteins such as Bim (Engel et al., 2011). In this context, transcriptional upregulation of Bim is required for apoptotic neuron death in response to NGF withdrawal and exposure to β-amyloid (Biswas et al., *J Biol Chem.* 282:29368-74, 2007; Biswas et al., J Neurosci. 27:893-900, 2007; Putcha et al., 2001; Whitfield et al., Neuron. 29:629-43, 2001).

Placing Caspase 2 within the above scheme has been problematic. Findings that Caspase 2 is activated by dimerization induced by interaction with signaling platforms that include the Caspase 2 binding adaptor protein RAIDD (Ahmad et al., Cancer Res. 57:615-9, 1997; Tu et al., Nat Cell Biol. 8:72-7, 2006), have indicated that it is an initiator caspase. However, other findings identify Caspase 2 as an effector that is downstream of other caspases (Samraj et al., Mol Biol Cell. 18:84-93, 2007; Van de Craen et al., Cell Death Differ. 6:1117-24, 1999). Similarly, some studies have suggested that activated Caspase 2 functions upstream of the apoptotic mitochondrial pathway while others consign it to a downstream (Slee et al., Cell Death Differ. 6:1067-74, 1999) or irrelevant role in apoptotic death (Guo et al., J Biol Chem. 277:13430-7, 2002; Ho et al., Oncogene. 27:3393-404, 2008; Shelton et al., J Biol Chem. 285:40525-33, 2010; Tiwari et al., J Biol Chem. 286: 8493-506, 2011). Until the studies presented herein, these issues have not been systematically addressed in neurons.

The present application includes studies addressing Caspase 2 activity in two different paradigms of neuron death: β-amyloid ($A\beta_{1-42}$) treatment and NGF (nerve growth factor) withdrawal. Specifically, the function and hierarchical role of Caspase 2 in the death signaling pathways triggered by these two apoptotic stimuli has been examined. Caspase 2 is shown to be rapidly activated in response to apoptotic stimuli and, surprisingly, promotes induction of Bim mRNA and protein. Moreover, this action is found to be mediated by Caspase 2-dependent activation of the transcription factor c-Jun. These findings causally associate Caspase 2, c-Jun and Bim in the same apoptotic pathway upstream of mitochondria and provide a novel mechanism by which activated Caspase 2 triggers neuron death.

Without being bound by theory, the instant invention is therefore directed, in certain embodiments, to methods of decreasing the risk or manifestation of neurodegenerative disease by administration of an inhibitor of Caspase 2 activation. For example, in certain embodiments, the instant invention is directed to methods of administering an effective amount of the Caspase 2 activation inhibitory peptide, or membrane permeable conjugate thereof, in order to treat a neurodegenerative condition.

In certain embodiments, the instant invention is directed to methods of administering an effective amount of the caspase 2 activation inhibitory peptide, or membrane permeable conjugated thereof, to inhibit $A\beta_1$ 42 and/or NGF induced cell death. In certain embodiments, such inhibition of $A\beta_{1-}42$ and/or NGF induced cell death by an effective amount of the caspase 2 activation inhibitory peptide, or membrane permeable conjugated thereof, is part of a treatment of a neurodegenerative condition.

In certain embodiments, the instant invention is directed to methods of administering an effective amount of a caspase 2 activation inhibitory peptide, or membrane permeable conjugated thereof, to inhibit Bim induction. In certain embodiments, such inhibition of Bim induction by an effective amount of the caspase 2 activation inhibitory peptide, or membrane permeable conjugated thereof, is part of a treatment of a neurodegenerative condition.

In certain embodiments, the instant invention is directed to methods of administering an effective amount of a caspase 2 activation inhibitory peptide, or membrane permeable conjugated thereof, to inhibit c-Jun induction. In certain embodiments, such inhibition of c-Jun induction by an effective amount of the caspase 2 activation inhibitory peptide, or membrane permeable conjugated thereof, is part of a treatment of a neurodegenerative condition.

In certain specific, non-limiting examples of the instant invention, AFDAFC-Pen1 is employed to inhibit $A\beta_1$42 and/or NGF induced cell death and/or induction of Bim, and/or c-Jun induction. In certain embodiments, AFDAFC-Pen1 is employed to treat a neurodegenerative disease. In certain of such examples, the AFDAFC-Pen1 is administered to a patient suffering from a neurodegenerative disease either as a single dose or in multiple doses. Where multiple doses are administered, they may be administered at intervals of 6 times per 24 hours or 4 times per 24 hours or 3 times per 24 hours or 2 times per 24 hours. The initial dose may be greater than subsequent doses or all doses may be the same. The concentration of the AFDAFC-Pen1 composition administered is, in certain embodiments: 0.01 µM to 1000 µM; 1 µM to 500 µM; or 10 µM to 100 µM. The AFDAFC-Pen1 composition is delivered nasally by administering, in certain embodiments, drops of 0.1 µl to 1000 µl; 1.0 µl to 500 µl; or 10 µl to 100 µl to alternating nares every 30 seconds to five minutes; every one minute to every four minutes; or every two minutes for 10 to 60 minutes; every 15 to 30 minutes; or every 20 minutes. In certain embodiments, a specific human equivalent dosage can be calculated from animal studies via body surface area comparisons, as outlined in Reagan-Shaw et al., FASEB J., 22; 659-661 (2007).

In certain embodiments of the instant invention, the Caspase 2 activation inhibitory peptide, or membrane-permeable complex thereof, is administered in conjunction with one or more additional therapeutics. In certain of such embodiments the additional therapeutics include, but are not limited to: Aβ "vaccines", which stimulate the immune system to produce antibodies to Aβ; Aβ antibodies, such as bapineuzumab; gamma secretase inhibitors, such as LY451039; and gamma secretase modulators, such as Tarenflurbil.

6. EXAMPLES

6.1 AFDAFC-Pen1 Abrogates AD-mediated Cell Death

Peptide Preparation: AFDAFC (SEQ ID NO: 1) was synthesized by Multiple Peptide Systems (San Diego, Calif.). Lyophilized peptide was resuspended in sterile ddH$_2$O and linked in equimolar amounts with Pen1 (Troy et al. Proc. Natl. Acad. Sci. U.S.A. 93: 5635-5640 (1996)) for a stock concentration of 80 µM. AFDAFC-Pen1 was used at a final concentration of 80 nM.

Primary Hippocampal Neuron Cultures:

Embryonic day 18 rat fetuses were removed from $CO_2$-sacrificed pregnant Sprague Dawley rats (Charles River). The hippocampus was dissected out from surrounding tissue and the meninges completely removed. Pooled tissue was mechanically dissociated in a serum-free defined medium. Medium consisted of a 1:1 mixture of Eagle's MEM and Ham's F12 (Invitrogen) supplemented with glucose (6 mg/ml), insulin, selenium (30 nM), progesterone (20 nM), transferrin (100 µg/ml), putrescine (60 µg/ml), penicillin (0.5 U/ml), and streptomycin (0.5 µg/ml). Dissociated cells were grown in poly-D-lysine and laminin-coated plates or 8-well chamber slides. Neurons were cultured for 7 days prior to experimental treatments.

β-Amyloid Preparation:

Lyophilized and HPLC-purified β-amyloid$_{1-42}$ (Aβ$_{1-42}$) was purchased from Dr. David Teplow (UCLA). Peptides were prepared according to (Fa et al., 2010) except that monomerized Aβ$_{1-42}$ was reconstituted in DMSO to 1 mM. To form Aβ$_{1-42}$ aggregates stocks of 1 mM were resuspended in PBS to a concentration of 100 µM and incubated at 37° C. for 24 hrs.

Caspase 2 Activity Assay:

50 µM of bVAD-fink, a biotinylated pan-caspase inhibitor that traps active caspases, was added to neurons 2 hrs prior to Aβ$_{1-42}$ stimulation. Cells were lysed in CHAPS buffer. Active caspase-bVAD-fink complex was pullout with streptavidin-coated beads (Invitrogen). Active Caspase 2 was determined by Western blotting using affinity purified polyclonal Caspase 2 antibody (Troy et al. J Neurosci. 17, 1911-1918, (1997).

6.2 Caspase 2 Regulates c-Jun Transcriptional Activation of Bim in Neuron Death

Bim and Caspase 2 Proteins are Elevated and Co-Expressed in Neurons from Alzheimer's Disease Patients.

It has been previously shown in cellular models of AD that Aβ$_{1-42}$ induces Dim transcripts and that Aβ-induced neuronal death requires Bim as well as Caspase 2 (Biswas et al., J Neurosci. 27:893-900, 2007; Troy et al., J Neurosci. 20:1386-92, 2000). Additionally, it has been observed that Dim expression is elevated in entorhinal cortical neurons of AD patients (Biswas et al., J Neurosci. 27:893-900, 2007), a brain region that shows early degeneration in AD. To determine whether Caspase 2 might also be dysregulated along with Bim in AD, brain sections from 6 AD patients and 6 age-matched controls were co-immunostained for both proteins. Representative images are shown in FIG. 8. Increased expression in entorhinal cortical neurons was consistently found not only of Bim, but also of Caspase 2 (FIG. 8). Moreover, Bim and Caspase 2 co-localized substantially within the same entorhinal cortical neurons in AD brains (FIG. 8). In contrast, there was no increased expression of either protein in cerebellum, an area spared of AD pathology (data not shown).

Caspase 2 is Rapidly Activated by Exposure to Aβ$_{1-42}$ and by NGF Deprivation.

Figure 9A:
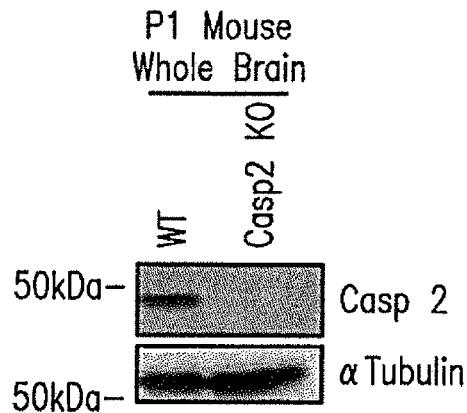

The required roles of Bim and Caspase 2 for neuron death in cellular models of AD and their increased expression and co-localization in AD neurons raised the possibility that they may function in the same apoptotic pathway. To assess a potential functional interaction between Bim and Caspase 2 in neuron death, primary cultures of rat hippocampal neurons were utilized. Hippocampal neurons undergo apoptotic death in response to treatment with Aβ$_{1-42}$, which requires both Bim (Biswas et al., J Neurosci. 27:893-900, 2007) and Caspase 2 (Troy et al., J Neurosci. 20:1386-92, 2000). A second, well-studied model of neuron death was also used: cultured sympathetic neurons deprived of NGF. In this system also, NGF deprivation induces elevation of Bim transcripts and protein and the subsequent neuron death requires both Bim (Biswas et al., J Biol Chem. 282:29368-74, 2007) and Caspase 2 expression (Troy et al., J Neurochem. 77:157-64, 2001; Troy et al., J Neurosci. 17:1911-8, 1997). The first aim was to detect Caspase 2 activation in these death models and to determine the time at which it occurs. To achieve this, an unbiased caspase activity probe (previously adapted for use in neurons) was employed (Akpan et al., 2011; Tizon et al., 2010). This approach involves a biotinylated pan-caspase inhibitor, bVAD-fink, which irreversibly binds and inhibits active caspases within cells and permits their subsequent isolation and identification by Western immunoblotting (Tu et al., 2006). When cells are pre-treated with bVAD-fink and then exposed to a death stimulus, bVAD binds to proximal caspases (usually initiator caspases) and inhibits their activation, usually that of initiator caspases. All subsequent events dependent on activity of the proximal caspases are blocked. The specificity of the polyclonal Caspase 2 antiserum used for these studies was confirmed by using brain lysates from wild-type and Caspase 2 null animals (FIG. 9A).

Figure 9B:
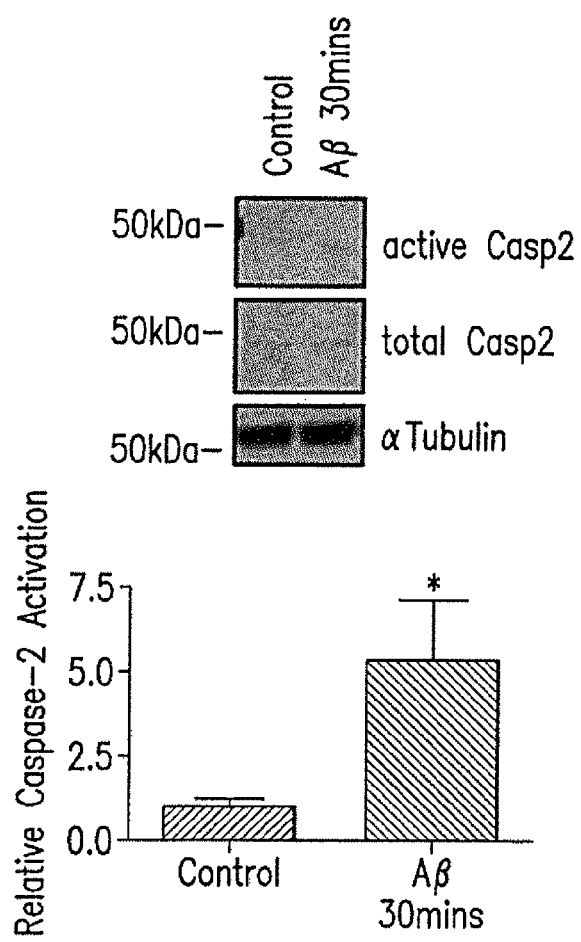
Figure 9C:
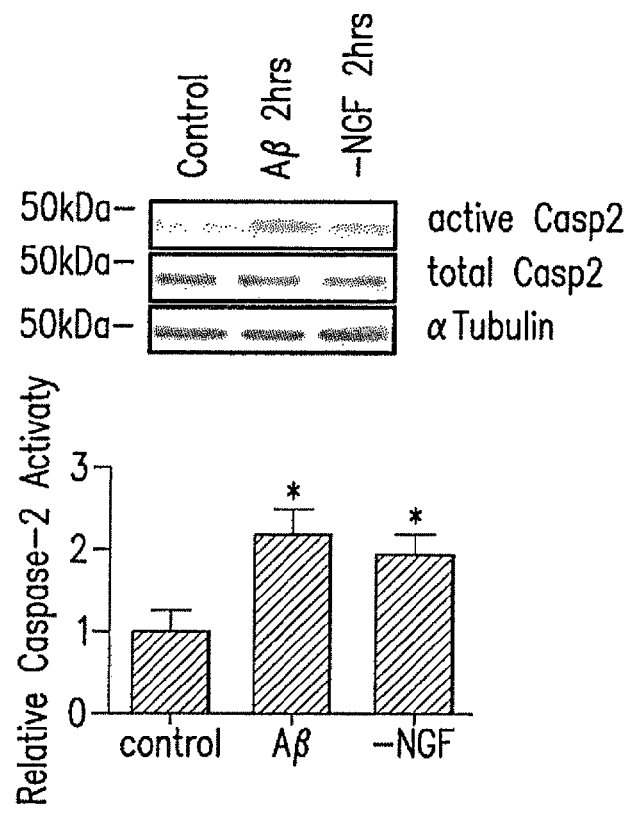

The levels of activated Caspase 2 in cultured hippocampal neurons significantly increased within 30 min of treatment with 3 µM Aβ$_{1-42}$ (FIG. 9B). Moreover, NGF withdrawal from sympathetic neurons elicited an increase in activated Caspase 2 within 2 hours (FIG. 9C). It has been reported that sympathetic neurons undergo apoptotic death in response to Aβ$_{1-42}$ and do so by a Caspase 2 dependent mechanism (Troy et al., J Neurosci. 20:1386-92, 2000). Consistent with this, Aβ$_{1-42}$ also activated Caspase 2 in sympathetic neurons within 2 hours (FIG. 9C). Total Caspase 2 levels remained unchanged in all models at these times (FIG. 9B,C). Taken together, these data show that Caspase 2 is rapidly activated in neurons in response to death stimuli; consistent with previous findings that neuronal apoptosis caused by Aβ$_{1-42}$ or NGF deprivation requires Caspase 2.

Bim Induction by Aβ$_{1-42}$ Occurs after Caspase 2 Activation.

Figure 9D:
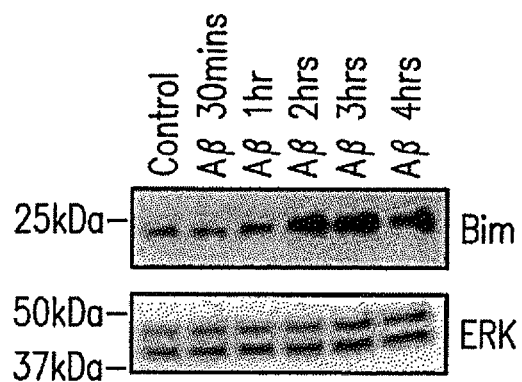

If Bim and Caspase 2 have the potential to function in the same apoptotic pathway, then it is important to determine the temporal relationship of Bim induction and Caspase 2 activation. In other models Bim elevation precedes activation of caspases such as caspases-9 and -3 (Strasser et al., Ann N Y Acad Sci. 917:541-8, 2000; Willis and Adams, Curr Opin Cell Biol. 17:617-25, 2005). Previous studies with hippocampal neurons indicated that Aβ$_{1-42}$. induces Bim mRNA within 1 hr, with a maximal effect at 3-6 hrs and that Bim protein is elevated within 4 hrs of treatment (Biswas et al., J Neurosci. 27:893-900, 2007). Therefore Bim protein expression was examined in hippocampal neuron cultures at relatively early times of Aβ$_{1-42}$ exposure, starting at 30 min (FIG. 9D). This revealed no change in Bim expression at 30 and 60 min but a significant increase by 2 hrs. These data (FIG. 9B,C) indicate that Caspase 2 activation occurs prior to Bim protein elevation and suggest that Caspase 2 activation is independent of Bim induction. The data also raised the possibility that activated Caspase 2 may be upstream of Bim regulation.

Caspase 2 Activation by Aβ$_{1-42}$ does not Require Bim Induction.

Figure 10A:
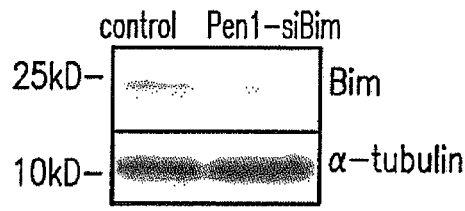
Figure 10B:
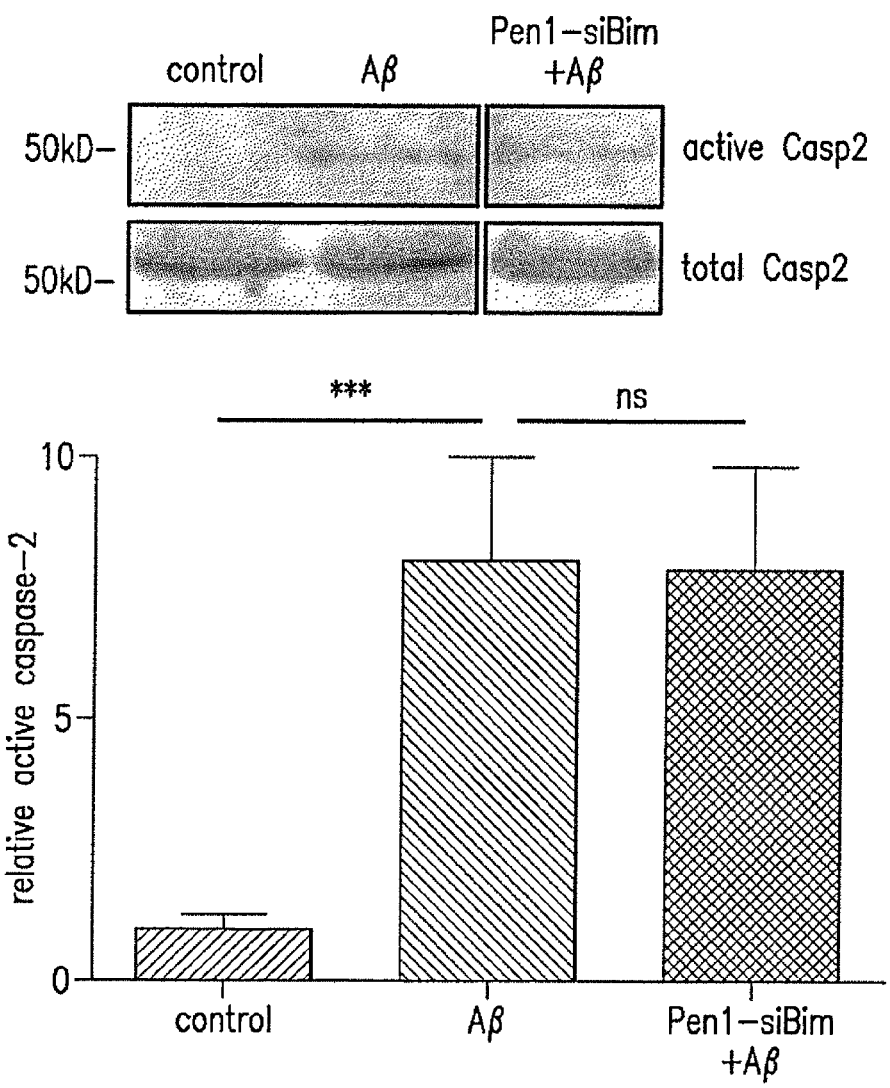

While the temporal data suggest that Caspase 2 activation could be upstream of Bim induction, the canonical pathway places Bim upstream of Caspase 2. To determine if Bim induction is required for Caspase 2 activation, a Bim specific siRNA conjugated to the cell penetrating peptide Penetratin1 (Pen1) was utilized for highly efficient, low toxicity delivery into neurons (Davidson et al., J Neurosci. 24:10040-6, 2004). This sequence has been previously used with an shRNA (Biswas et al., *J Biol Chem.* 282:29368-74, 2007) to suppress Bim expression and to provide protection from apoptotic stimuli and, as shown in FIG. 10A, found that 5 hrs treatment of cultured hippocampal neurons with Pen1-siBitn yielded substantial knockdown of Bim expression. Cultures of hippocampal neurons were preincubated with Pen1-siBim for 3 hrs and then bVAD-fmk was added for 2 hrs followed by addition of $A\beta_{1-42}$. After 4 hours of $A\beta_{1-}42$ exposure, the neurons were harvested and activated Caspase 2 was detected by Western immunoblotting. This revealed that knockdown of Bim did not alter the activation of Caspase 2 by $A\beta_{1-42}$ (FIG. 10B), thus indicating that Bim is not upstream of Caspase 2 activation in this model.

Bim Induction by $A\beta_{1-42}$ is Blocked by a Pan-Caspase Inhibitor.

Figure 10C:
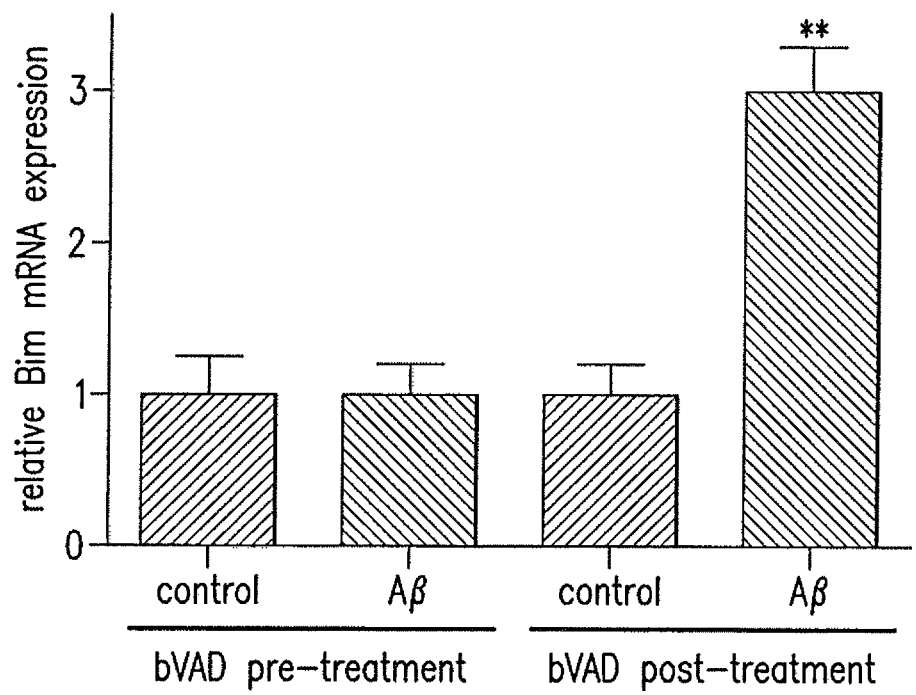
Figure 10D:
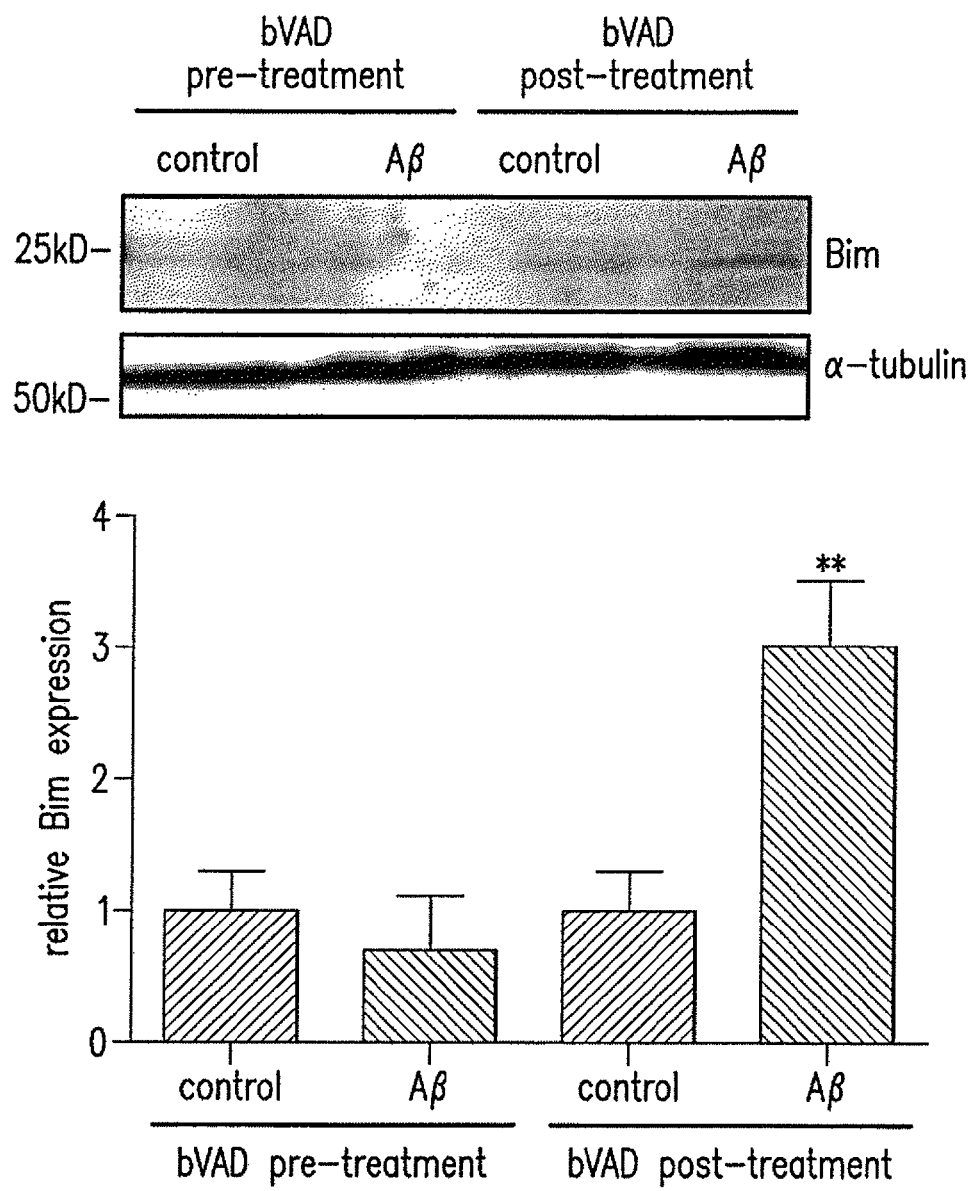
Figure 10E:
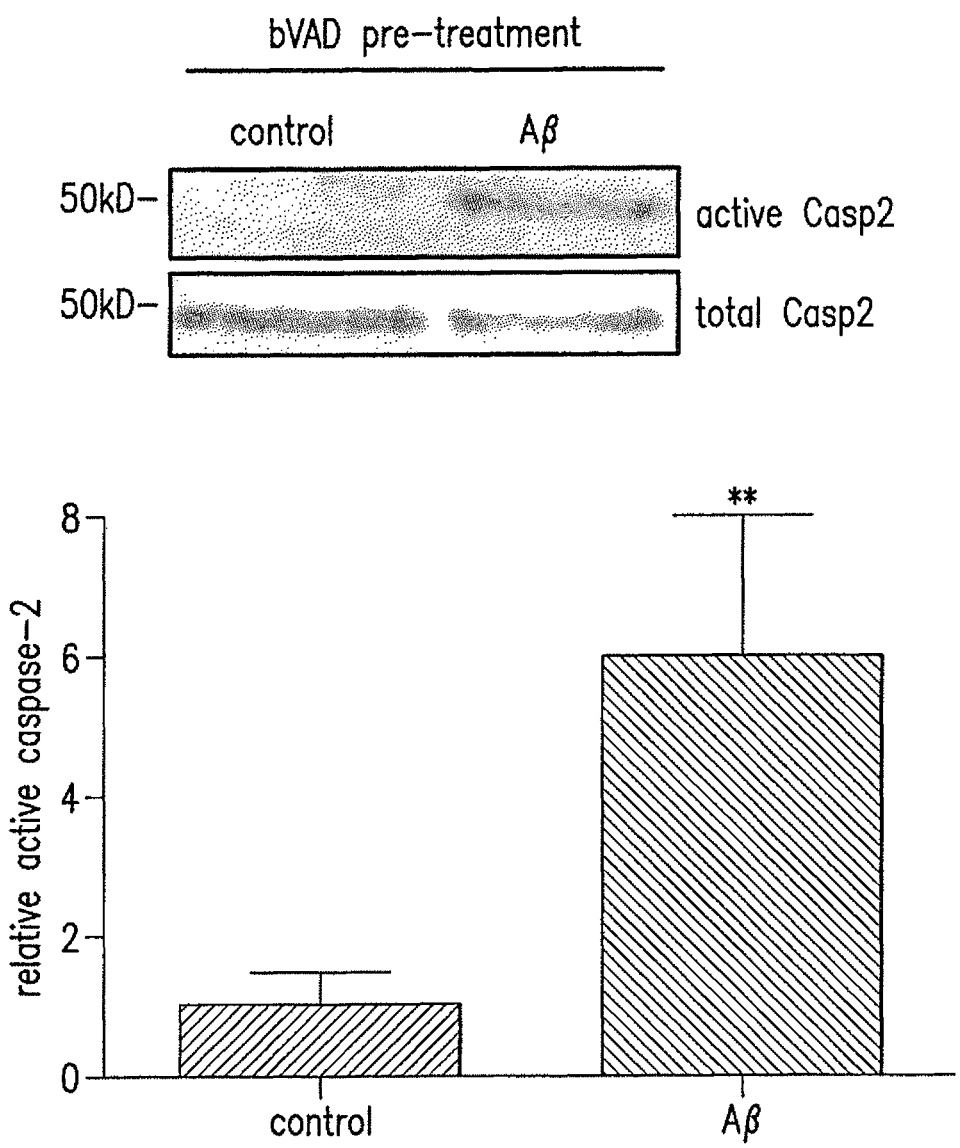

Since Bim does not appear to act upstream of Caspase 2 activation, consideration was made whether it may act downstream. As a first step to determine whether caspase activity is required for Bim induction, the pan-caspase inhibitor bVAD-fmk, which are shown above captures active Caspase 2, was utilized and should inhibit any subsequent action of Caspase 2 and any other captured caspases. Cultured hippocampal neurons were pretreated with bVAD-fink for 2 hrs followed by addition of $A\beta_{1-42}$ for another 4 hrs and were then assessed for Bim mRNA and protein levels. Caspase inhibition by bVAD-fink blocked induction of both Bim transcripts and protein (FIG. 10C,D). Western immunoblotting confirmed the capture of activated Caspase 2 under these conditions (FIG. 10E). In contrast, when bVAD-fmk was added two hours after $A\beta_{1-42}$, a time at which Caspase 2 has already been activated (FIG. 9B), induction of Bim mRNA and protein still took place (FIG. 10C,D). These findings indicate that caspase activation occurs upstream of Bim induction.

Induction of Bim mRNA and Protein by Apoptotic Stimuli Requires Caspase 2 Expression.

Figure 11A:
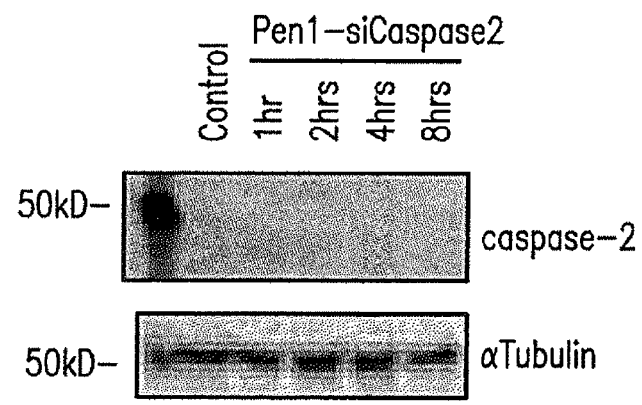
Figure 11B:
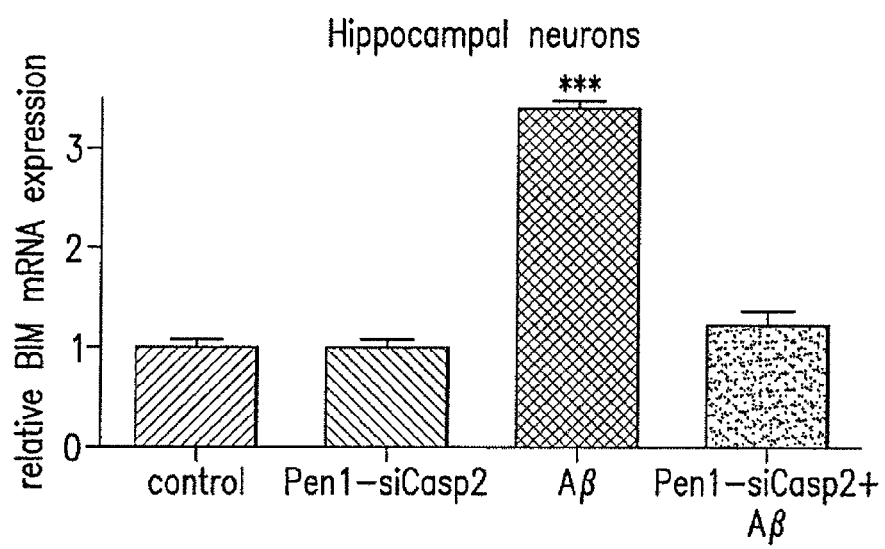
Figure 11C:
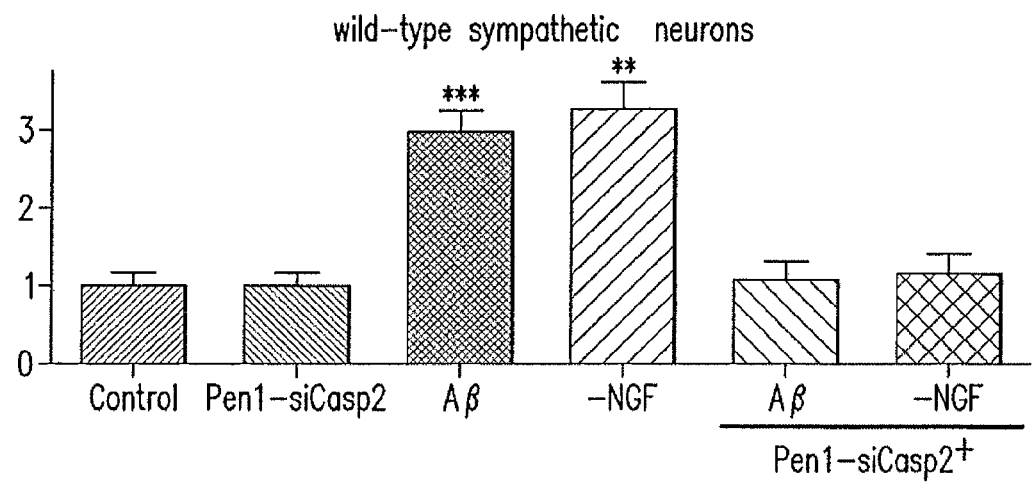
Figure 11D:
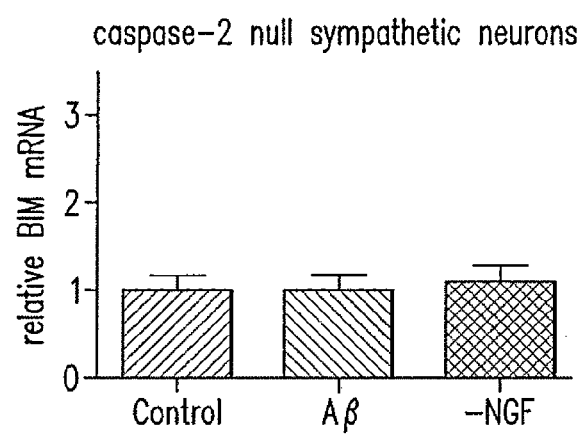
Figure 11E:
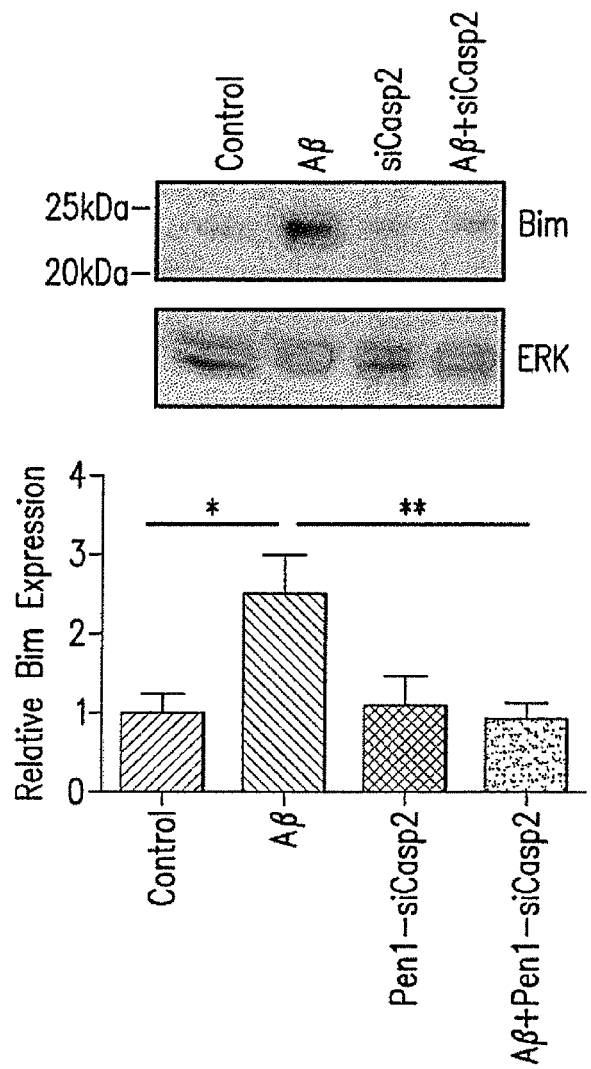

Whether Caspase 2 is specifically required for Bim induction was examined by apoptotic stimuli. A Caspase 2 specific siRNA conjugated to Pen1 was used in this study. In cultured hippocampal neurons knockdown of Caspase 2 with this reagent was evident within 2 hrs and appeared to be maximal by 4 hrs (FIG. 11A). Knockdown of Caspase 2 in these neurons completely blocked the induction of Bim mRNA that occurs after 4 hrs of $A\beta_{1-42}$ treatment (FIG. 11B). Similarly, Pen1-siCaspase 2 fully inhibited the capacity of $A\beta_{1-42}$ to induce Bim transcripts in cultured sympathetic neurons (FIG. 11C). Finally, Caspase 2 knockdown repressed Bim mRNA induction caused by NGF withdrawal from sympathetic neurons (FIG. 11C). Taken together, these data indicate that Caspase 2 expression is required for transcriptional regulation of Bim in two different apoptotic models and two different neuronal types. To further support this conclusion, sympathetic neurons cultured from Caspase 2 null mice were utilized. Bim mRNA was measured following 4 hrs of $A\beta_{1-42}$ treatment or NGF deprivation. In both paradigms, in contrast with sympathetic neurons from wild-type mice (FIG. 11C), Bim transcripts were unchanged in the Caspase 2 null neurons (FIG. 11D).

Figure 11F:
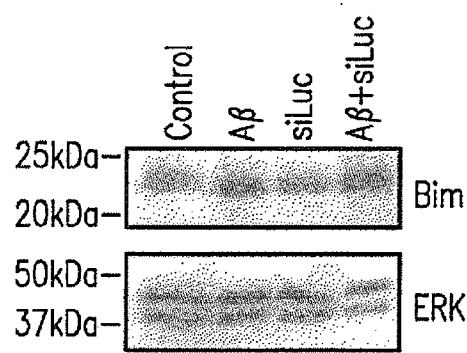
Figure 11G:
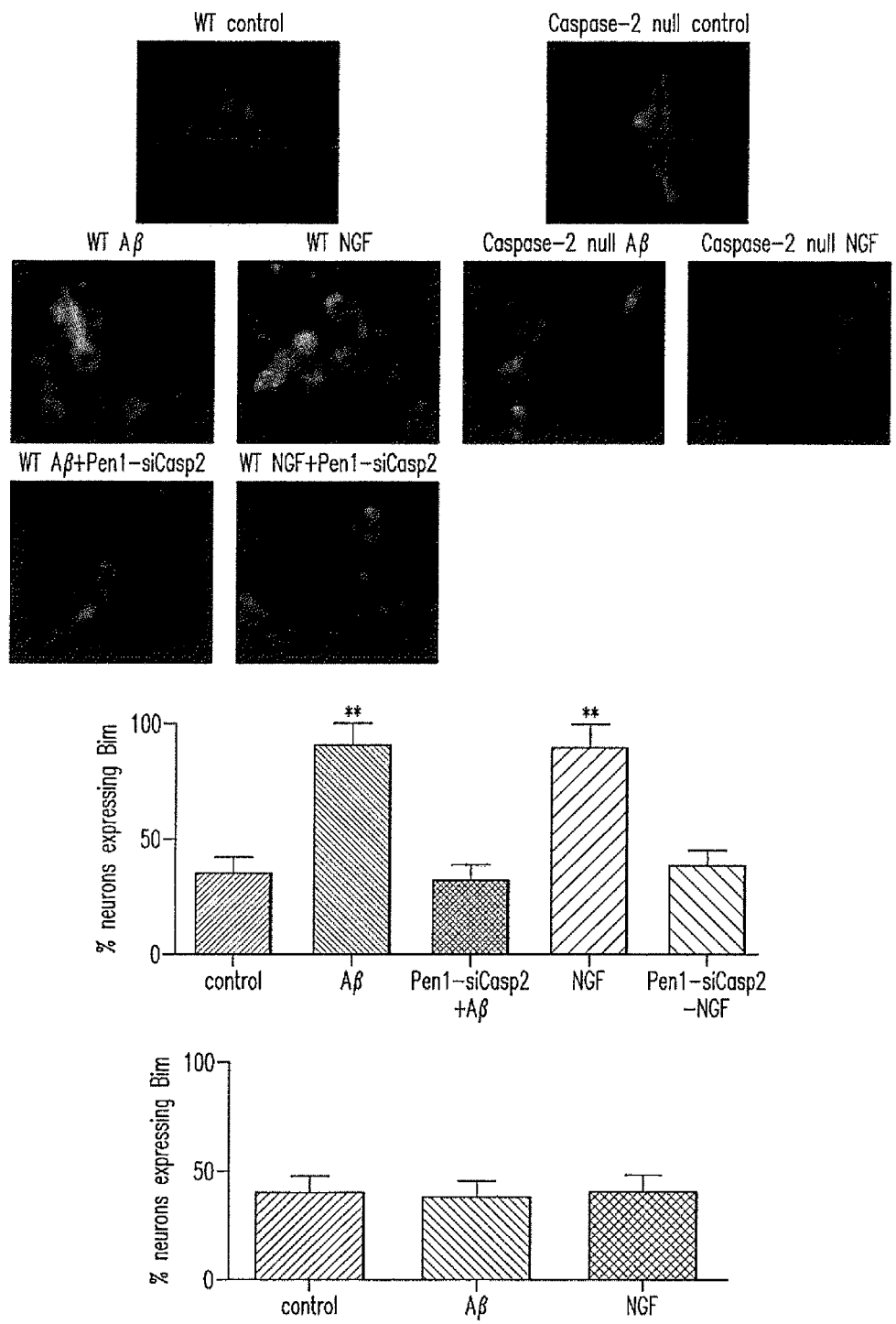

Parallel experiments were carried out to examine the role of Caspase 2 in the elevation of Bim protein levels by $A\beta_{1-42}$ and NGF deprivation. Pen1-siCaspase 2 fully inhibited the capacity of $A\beta_{1-42}$ to increase Bim protein expression in cultured hippocampal neurons (FIG. 11E) after 8 hrs of treatment. As a control, a Pen1-siRNA targeting the firefly luciferase gene was employed. In contrast with Pen1-siCaspase 2, this construct had no effect on the increase in Bim protein levels caused by $A\beta_{1-42}$ treatment (FIG. 11F). The effects of apoptotic stimuli on Bim protein expression in wild-type and Caspase 2 null sympathetic neurons were also compared. To achieve this, cultures (with and without $A\beta_{1-42}$ treatment or NGF deprivation for 5 hrs) were immunostained for Bim expression and scored in a blinded manner as previously described (Biswas et al., *J Biol Chem.* 282:29368-74, 2007) for proportion of neurons with high Bim staining. In cultures from wild-type animals, there was a substantial increase in the proportion of neurons that showed high Bim staining and this response was completely blocked by pretreatment with Pen1-siCaspase 2 (FIG. 11G). In contrast, apoptotic stimuli caused no significant change in Bim expression in Caspase 2 null neurons (FIG. 11G). Collectively, these findings indicate that Caspase 2 is required for induction of Bim mRNA and protein in neurons after $A\beta_{1-42}$ exposure and NGF deprivation.

Bim Induction by $A\beta_{1-42}$ Requires RAIDD Expression/Caspase 2 Activation.

The above studies indicate that caspase activity and Caspase 2 expression are necessary for Bim induction by $A\beta_{1-42}$ exposure or NGF deprivation. Next the question of whether such induction requires Caspase 2 activation was specifically addressed. To do so, advantage was taken of prior findings that Caspase 2 activation requires the death adapter RAIDD (Duan and Dixit, Nature. 385:86-9, 1997; Ribe et al., Biochem. J., In Press, 2012; Wang et al., Cell Death Differ. 13:75-83, 2006). RAIDD expression is also necessary for neuron death caused by NGF deprivation (Ribe et al., Biochem. J., In Press 2012; Wang et al., Cell Death Differ. 13:75-83, 2006) and $A\beta_{1-42}$ treatment (Ribe et al., Biochem. J., In Press, 2012). A Penetratin-1-linked RAIDD siRNA (Pen1-siRAIDD) was used that effectively knocks down RAIDD mRNA and protein levels in cultured hippocampal neurons (FIG. 12A) and that protects hippocampal neurons from death induced by $A\beta_{1-42}$ (Ribe et al., Biochem. J., In Press, 2012). Simultaneous treatment with Pen1-siRAIDD suppressed the induction of Bim protein elicited by 8 hrs of exposure to $A\beta_{1-42}$ (FIG. 12B).

Further establishing the relationship of RAIDD and Caspase 2 in the context of $A\beta_{1-42}$-induced activation, AFDAFC-Pen1 is shown to reduce $A\beta_{1-42}$-induced binding of Caspase 2 to RAIDD. FIG. 13 depicts a Western blot showing levels of Caspase 2 bound to endogenous RAIDD in control conditions, in the presence of $A\beta_{1-42}$, in the presence of AFDAFC-Pen1, and in the presence of $A\beta_{1-42}$ and AFDAFC-Pen1 in primary hippocampal neurons. The level of Caspase 2 bound to endogenous RAIDD increased in $A\beta_{1-42}$-treated cells. This increase was not seen in cells treated with AFDAFC-Pen1 prior to $A\beta_{1-42}$ treatment.

A second study employing AFDAFC-Pen1 establishes that administration of AFDAFC-Pen1 Caspase 2 inhibitor is similarly capable of preventing Bim induction elicited by exposure $A\beta_{1-42}$. FIG. 14 depicts the results of a Western blot showing levels of Bim in control conditions, in the presence of $A\beta_{1-42}$, in the presence of AFDAFC-Pen1, and in the presence of $A\beta_{1-42}$ and AFDAFC-Pen1 in primary hippocampal neurons. The level of Bim increased in cells treated with $A\beta_{1-42}$. This increase was not seen in cells treated with AFDAFC-Pen1 prior to $A\beta_{1-42}$. Thus, this study confirms that RAIDD expression and therefore Caspase 2 activation are required for Bim induction by $A\beta_{1-42}$, and that AFDAFC-Pen1 is capable of inhibiting Caspase 2 activation, and Bim induction, normally associated with exposure to $A\beta_{1-42}$.

Caspase 2 Acts Upstream of Bim Induction by Enabling Activation of c-Jun.

Bim induction by apoptotic stimuli requires transcriptional activation that can be mediated by a variety of transcription factors (Biswas et al., J Biol Chem. 282:29368-74, 2007;

Gilley et al., J Cell Biol. 162:613-22, 2003; Hughes et al., Cell Death Differ. 18:937-47, 2011; Xie et al., J Neurosci. 31:5032-44, 2011). Therefore, whether Caspase 2 might function upstream of transcription factor activation was examined. c-Jun was focused on as it has been reported to be elevated in neurons from AD patients and it is activated in response to a cascade of phosphorylation events set in motion by $A\beta_{1-42}$ treatment (Troy et al., J Neurochem. 77:157-64, 2001). Inhibition of this phosphorylation cascade blocks both $A\beta_{1-42}$-mediated Bim induction as well as neuron death (Biswas et al., J Biol Chem. 282:29368-74, 2007; Troy et al., J Neurochem. 77:157-64, 2001).

To assess the potential role of Caspase 2 in c-Jun activation, hippocampal neurons were treated with $A\beta_{1-42}$ for 8 hrs in the presence or absence of Pen1-siCaspase 2 and carried out Western immunoblots to detect phospho-c-Jun. $A\beta_{1-42}$ caused robust phosphorylation of c-Jun, which was significantly inhibited by Pen1-siCaspase 2 (FIG. 15A), and by Pen1-siRAIDD (FIG. 15B). Complementary experiments were conducted to assess the effects of Pen1-siCaspase 2 and Pen1-siRAIDD on $A\beta_{1-42}$ induction of nuclear phospho-c-Jun. Hippocampal neuron cultures were treated with or without the two Pen-1 siRNAs and with or without $A\beta_{1-42}$ for 8 hrs, immunostained with anti-phospho-c-Jun and then blindly assessed for proportions of neurons with strong nuclear staining for phospho-c-Jun. $A\beta_{1-42}$ alone elicited a large increase in proportions of neurons exhibiting strong nuclear phospho-c-Jun immunostaining, which was fully blocked in the presence of Pen1-siCaspase 2 or Pen1-siRAIDD (FIG. 15C). These findings indicate that Caspase 2 expression, as well as Caspase 2 activation, is required for c-Jun phosphorylation/activation and nuclear localization in response to $A\beta_{1-42}$. These observations illustrate at least one mechanism by which Caspase 2 promotes Bim induction, and demonstrate that activated Caspase 2 participates in c-Jun activation in response to an apoptotic stimulus.

Caspase 2 is required for Bim induction in an animal model of AD pathology. To extend the above-described in vitro studies, whether Caspase 2 also regulates Bim in an in vivo animal model of AD pathology was determined. Previous studies have shown that infusion of $A\beta_{1-42}$ into the hippocampus causes neurodegeneration by 2 weeks (Sotthibundhu et al., J Neurosci. 28:3941-6, 2008). $A\beta_{1-42}$ (0.4 nmoles) or vehicle alone was infused via convection enhanced delivery (CED) (FIG. 16A) (Akpan et al., J Neurosci. 31:8894-904, 2011) into the right hippocampi of 16-month-old wild-type (n=8) and Caspase 2 null mice (n=8). The animals were sacrificed two weeks later and the brains prepared for Fluoro-Jade B and Bim immunohistochemical staining. Consistent with the previously described role of Caspase 2 in neuron death caused by $A\beta_{1-42}$ in vitro (Troy et al., J Neurosci. 20:1386-92, 2000), Fluoro-Jade B staining revealed evidence of neurodegeneration in wild-type but not in Caspase 2 null brains injected with $A\beta_{1-42}$ (FIG. 16B), Immunostaining of brains from wild-type mice showed a robust increase in Bim expression within cortical neurons near the site of infusion for animals receiving $A\beta_{1-42}$ compared with those infused with vehicle alone (FIG. 16C). Interestingly, no such increase occurred in brains of Caspase 2 null mice infused with $A\beta_{1-42}$ (FIG. 16C). Taken together, these findings confirm Bim induction in an animal model of AD pathology and indicate that in this model, Caspase 2 and Bim up-regulation are required for neurodegeneration.

Materials & Methods.

Cell Culture of primary hippocampal neuron cultures. Neurons were cultured as previously described (Akpan et al., J Neurosci. 31:8894-904, 2011). Briefly, embryonic day 18 rat fetuses were removed from CO2-sacrificed pregnant Sprague Dawley rats (Charles River). The hippocampus was dissected from surrounding tissue and the meninges removed. Pooled hippocampi were mechanically dissociated in a serum-free defined medium. Medium consisted of a 1:1 mixture of Eagle's MEM and Ham's F12 (Invitrogen) supplemented with glucose (6 mg/ml), insulin (25 µg/ml), selenium (30 nM), progesterone (20 nM), transferrin (100 µg/ml), putrescine (60 µg/ml), penicillin (0.5 U/ml), and streptomycin (0.5 µg/ml). Dissociated cells were grown on poly-D-lysine coated plates or 8-well chamber slides. Neurons were cultured for 7 days prior to experimental treatments.

Primary sympathetic neuron cultures. Neurons were cultured as previously described (Troy et al., J Neurochem. 77:157-64, 2001). Briefly, sympathetic neurons were dissected from 1-day-old wild-type and Caspase 2 null (Bergeron et al., Genes Dev. 12:1304-14, 1998) mouse pups. Cultures were maintained in RPMI 1640 medium supplemented with 10% horse serum and mouse NGF (100 ng/ml) on collagen-coated 24-well dishes. For cells that were subjected to microscopic imaging, Matrigel-coated 8-well chamber slides were used. One day after plating, uridine (10 µM) and 5-fluorodeoxyuridine (10 µM) were added for 3 days to eliminate non-neuronal cells. Experiments were conducted after 6 days of culture.

Cell Survival Assay. Hippocampal or sympathetic neuron survival was scored as previously reported (Troy et al., J Neurosci. 17:1911-8, 1997). For hippocampal neurons, culture medium was removed by aspiration and 100 µl of detergent-containing lysis solution was added to the well. This solution dissolves cell membranes providing a suspension of intact nuclei. Intact nuclei were quantified using a hemacytometer. Triplicate wells were scored and values reported as mean±SEM. Significance was calculated by Student's t-test. For sympathethic neurons, each culture was scored as numbers of living, phase-bright neurons counted in the same field at various times. Three replicate cultures were assessed for each condition, and data are normalized to numbers of neurons present in each culture at the time of Aβ1-42 addition or NGF deprivation and reported as mean±SEM.

β-amyloid Preparation. Lyophilized and HPLC-purified β-amyloid1-42 (Aβ1-42) was purchased from Dr. David Teplow (UCLA). Peptides were prepared according. to Fa et al. (Fa et al., J Vis Exp 2010) except that monomerized Aβ1-42 was reconstituted in DMSO to 1 mM. To form Aβ1-42 aggregates stocks of 1 mM peptide were resuspended in PBS to a concentration of 100 µM and incubated at 37° C. for 24 hrs. 3 µM Aβ1-42 was used in all experiments.

siRNA Conjugation and Use. siRNAs against Caspase 2 and RAIDD were generated (Dharmacon). The sequence for Caspase 2 is: GCCAUGCACUCCUGAGUUU (SEQ ID NO: 11). The sequence for RAIDD is: CCACAUUCAAGAAAU-CAAA (SEQ ID NO: 12). The siRNAs were customized with a thiol group attached to the 5' ends of the sense strands. Prior to use each siRNA sequence was conjugated to Penetratin1 (Pen1) (Davidson et al., J Neurosci. 24:10040-6, 2004). Penetratin1-linked siRNA allows efficient delivery of siRNA into cells with minimal toxicity. For experiments all Pen1-siRNA were used at 80 nM.

Western Blot. Hippocampal neurons or sympathetic neurons were lysed in CHAPS lysis buffer (150 nM KCl, 50 mM HEPES, 0.1% CHAPS, protease inhibitor tablet, pH 7.4). Protein concentration was determined using BioRad protein assay reagent (Bio-Rad). Equal amounts of protein were loaded onto 10% or 12% polyacrylamide gels. The proteins were transferred onto nitrocellulose transfer membranes (Millipore). Subsequently, the membranes were blocked in 5% milk for 1 hr. Primary antibodies used for Western immunoblots include Caspase 2 (Affinity purified, 1:250), phospho-cJun (Ser63) (Cell Signaling, 1:750), dun (Cell Signaling, 1:750), ERKI (Santa Cruz, 1:10,000), αTubulin (Abeam, 1:10,000), or Bim (Cell Signaling, 1:1,000). Proteins were detected using either enhanced chemiluminescence (Thermo Scientific) or fluorescence using the Odyssey infrared imaging system (LI-COR Biosciences). The relative densities of immunopositive bands were analyzed using ImageJ.

Real Time PCR (RT-PCR). Hippocampal or sympathetic neuron cultures grown in 24-well plates were harvested using iced cold 100% Trizol reagent (Invitrogen). cDNA was transcribed from RNA using Superscript RT II (Invitrogen). Equal amounts of cDNA were used for each PCR reaction for Bim, □□tubulin. The sequence for the rat specific Bim primer was published previously (Biswas et al., J Neurosci. 27:893-900, 2007). cDNA was added to 25 µl of reaction mixture containing OmniMix HS master mix (Cepheid) and SYBR Green I (Invitrogen) together with appropriate primers. Quantitative PCR was performed using a Cepheid Smart-Cycler according to the manufacturer's directions.

Caspase 2 Activity Assay. This unbiased Caspase 2 activity measurement was adapted from (Tu et al., 2006). 50 µM of bVAD-fink, a biotinylated pan-caspase inhibitor that traps active caspases, was added to neuronal cultures 2 hrs prior to $A\beta 1$-42 or NGF deprivation. Cells were lysed in CHAPS buffer. Active caspase-bVAD-fink complex was pulled out with streptavidin-coated beads (Invitrogen). Active Caspase 2 was detected by Western blotting using affinity purified polyclonal Caspase 2 antibody (Troy et al., J Neurosci. 17:1911-8, 1997).

Caspase 2 and RAIDD Co-Immunoprecipitation (IP). Mouse IgG magnetized beads (Invitrogen) were pre-coated with a RAIDD antibody (anti-CRADD; Abnova) for 2 hrs at 4° C. on a rotator. 2 µg of antibody was used per 30 µl of beads. Primary rat hippocampal neurons were treated with $A\beta_{1-42}$ (3 µM) for 1 or 2 hrs. Cell lysates were prepared using CHAPS lysis buffer. 70-120 µg of lysates were loaded onto anti-CRADD pre-coated beads and incubated overnight at 4° C. on a rotator. Following the overnight incubation, the captured proteins were boiled off the beads at 100° C. for 5 mins. The immunoprecipitated samples, along with inputs, were then subjected to Western blotting using affinity purified polyclonal anti-Caspase 2.

Immuno-staining. Immunocytochemistry. E18 rat hippocampal neurons and P1 mouse sympathetic neurons were cultured on 8-well chamber slides (Nunc) for 1 week. Cultures were then fixed in a solution of 3.7% formaldehyde and 5% sucrose at 37° C. for 20 min. The cells were rinsed in TRIS buffer saline (TBS). Cultures were blocked in TBS supplemented with 3% normal goat serum (NGS) for at least 1 hr at RT. Primary antibodies used include anti-phosho-cJun (Ser63) (1:100, Cell Signaling) and anti-βIII-Tubulin (1:1000, Abeam).

Immunohistochemistry. Frozen mouse and human brain tissue sections were washed in PBS for 15 mins and then blocked in PBS with 1% bovine serum albumin (BSA), 10% NGS, and 0.5% Triton X-100 for 1 hr. Primary antibodies used include anti-Bim (1:100, Cell Signaling) and anti-Caspase 2 (1:100, affinity purified). To prevent autofluorescence 1% sudan black (prepared in 70% EtOH) was used to treat the sections for 5 mins prior to cover-slip mount.

Flouro-Jade B Labeling. Frozen mouse brain sections were air dried at 45° C. for 20 mins. Slides were incubated in 1% NaOH+80% EtOH for 5 mins, followed by a 2 mins rinse in 70% EtOH and a 2 mins rinse in water. Sections were then incubated in 0.06% potassium permanganate for 10 mins, and subsequently incubated with 0.0004% flouro-jade B (made in 0.1% acetic acid) for 30 mins. Finally, water washes, followed by air drying for 5 mins at 50° C., and then mounted with permount.

Mouse Hippocampal Aβ1-42 Infusion. Adult wild-type or Caspase 2 null male mice were used. Mice were anesthetized with Avertin (2, 2, 2 tribromoethanol, 0.8 mg/g, Sigma-Aldrich) and then place onto a stereotaxic frame. The coordinates from Bregma 2.45 mm AP, 1.5 mm ML, and 1.7 mm DV were used to drill a hole into the skull and then a Hamilton syringe was inserted into the right CA1 region of the hippocampus. 4 µl of Aβ1-42 (100 µM) was infused via convection enhanced delivery (CED) at a rate of 0.2 it per minute. Following injection, the head wound was closed using Vetbond (3M) and the animals were maintained for 2 weeks.

Mouse Brain Processing and Sectioning. After the 2 week survival period animals were anaesthetized with 1:5 xylazine: ketamine and transcardiacally perfused with 4% paraformaldehyde. Brains were removed and post-fixed with 4% paraformaldehyde for 24 hrs at 4° C., followed by 30% sucrose infiltration. The brains were embedded in Optimal Cutting Temperature embedding medium (Tissue-Tek) and stored at −80° C. For immunohistochemistry, brains were sectioned on a cryostat at 15 µm thickness and mounted onto SuperfrostPlus slides.

Microscopy. Both in vitro and in vivo immunostainings were visualized using PerkinElmer spinning disc confocal, 40× or 60× magnification.

Various patents, patent application, and publications are cited herein, the contents of which are hereby incorporated in their entireties

What is claimed is:

1. A Caspase 2 activation inhibitor composition consisting of the amino acid sequence AFDAFC (SEQ ID NO: 1) conjugated to a cell penetrating peptide selected from the group consisting of Penetratin1, transportan, pIS1, Tat(48-60), pVEC, R16, RVGRRRRRRRRR (SEQ ID NO: 4), MPS, and KLALKLALKALKAALKLA-amide (SEQ ID NO: 10).

2. The composition of claim 1, wherein the cell-penetrating peptide is Penetratin1.

3. A method of treating a neurodegenerative condition comprising administering, intranasally, an effective amount of a Caspase 2 activation inhibitor composition consisting of the amino acid sequence AFDAFC (SEQ ID NO: 1) conjugated to a cell penetrating peptide selected from the group consisting of Penetratin1, transportan, pIS1, Tat(48-60), pVEC, R16, RVGRRRRRRRRR (SEQ ID NO: 4), MPS, and KLALKLALKALKAALKLA-amide (SEQ ID NO: 10) to a subject in need thereof, wherein the neurodegenerative condition is treated by such administration.

4. The method of claim 3, wherein the neurodegenerative condition is selected from the group consisting of: Alzheimer's Disease, Mild Cognitive Impairment, Parkinson's Disease, amyotrophic lateral sclerosis, Huntington's chorea, and Creutzfeld-Jacob disease.

5. A method of inhibiting a neurodegenerative condition associated with apoptosis in the central nervous system comprising administering, intranasally, an effective amount of the Caspase 2 activation inhibitor composition consisting of the amino acid sequence AFDAFC (SEQ ID NO: 1) conjugated to a cell penetrating peptide selected from the group consisting of Penetratin1, transportan, pIS1, Tat(48-60), pVEC, R16, RVGRRRRRRRRR (SEQ ID NO: 4), MPS, and KLALKLALKALKAALKLA-amide (SEQ ID NO: 10) to a subject in need thereof.

6. The method of claim 5, wherein the cell-penetrating peptide is Penetratin1.

\* \* \* \* \*

SEQUENCE LISTING

```
<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Phe Asp Ala Phe Cys
1               5
```

```
<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term OH

<400> SEQUENCE: 3

Arg Arg Leu Arg Arg Leu Leu Arg Arg Leu Leu Arg Arg Leu Arg Arg
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Val Gly Arg Arg Arg Arg Arg Arg Arg Arg Arg
1               5                   10

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Val Ile Arg Val Trp Phe Gln Asn Lys Arg Cys Lys Asp Lys Lys
1               5                   10                  15

<210> SEQ ID NO 7
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Lys Lys Arg Arg Gln Arg Arg Arg
1               5

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Leu Ile Ile Leu Arg Arg Arg Ile Arg Lys Gln Ala His Ala His
1               5                   10                  15

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amide

<400> SEQUENCE: 10

Lys Leu Ala Leu Lys Leu Ala Leu Lys Ala Leu Lys Ala Ala Leu Lys
1               5                   10                  15

Leu Ala

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gccaugcacu ccugaguuu                                              19

<210> SEQ ID NO 12
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 12
ccacauucaa gaaaucaaa                                                    19
```